(12) United States Patent
Strano et al.

(10) Patent No.: US 11,698,372 B2
(45) Date of Patent: Jul. 11, 2023

(54) NEAR INFRARED FLUORESCENT BIOSENSORS FOR STEROID HORMONES

(71) Applicant: MASSACHUSETTS INSTITUTE OF TECHNOLOGY, Cambridge, MA (US)

(72) Inventors: Michael Strano, Lexington, MA (US); Michael Lee, Carteret, NJ (US); Naveed Bakh, Lexington, KY (US); Song Wang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 377 days.

(21) Appl. No.: 16/866,091

(22) Filed: May 4, 2020

(65) Prior Publication Data
US 2020/0348291 A1    Nov. 5, 2020

Related U.S. Application Data

(60) Provisional application No. 62/843,544, filed on May 5, 2019.

(51) Int. Cl.
| G01N 33/543 | (2006.01) |
| G01N 33/74 | (2006.01) |
| A61B 5/145 | (2006.01) |
| A61B 5/1459 | (2006.01) |

(52) U.S. Cl.
CPC ... *G01N 33/5436* (2013.01); *G01N 33/54393* (2013.01); *G01N 33/743* (2013.01); *A61B 5/1459* (2013.01); *A61B 5/14546* (2013.01); *A61B 2562/0238* (2013.01); *A61B 2562/0285* (2013.01)

(58) Field of Classification Search
CPC .......... G01N 33/743; G01N 33/54393; G01N 33/5436
See application file for complete search history.

(56) References Cited

U.S. PATENT DOCUMENTS

2005/0227258 A1* 10/2005 Bright .................. G01N 33/543
435/7.1

OTHER PUBLICATIONS

Gili Bisker, "A Mathematical Formulation and Solution of the CoPhMoRe Inverse Problem for Helically Wrapping Polymer Corona Phases on Cylindrical Substrates", American Chemical Society, 2015 (Year: 2015).*
Bin Mu, "Recent Advances in Molecular Recognition Based on Nanoengineered Platforms", American Chemical Society, 2014 (Year: 2014).*
Shangchao Lin, "Understanding Selective Molecular Recognition in Integrated Carbon Nanotube-Polymer Sensors by Simulating Physical Analyte Binding on Carbon Nanotube-Polymer Scaffolds", 2014. (Year: 2014).*
Jingqing Zhang, "Molecular recognition using nanotube-adsorbed polymer phases: nanotube antibodies", Nat Nanotechnol. Dec. 2013. (Year: 2013).*

* cited by examiner

*Primary Examiner* — Maurice C Smith
(74) *Attorney, Agent, or Firm* — Honigman LLP

(57) ABSTRACT

Corona Phase Molecular Recognition (CoPhMoRe) utilizing a template heteropolymer adsorbed onto and templated by a nanoparticle surface to recognize a specific target analyte can be used for macromolecular analytes, including proteins.

23 Claims, 18 Drawing Sheets

NEAR INFRARED FLUORESCENT BIOSENSORS FOR STEROID HORMONES

CLAIM OF PRIORITY

This application claims priority to U.S. Provisional Patent Application No. 62/843,544, filed May 5, 2019, which is incorporated by reference in its entirety.

FEDERAL SPONSORSHIP AND GOVERNMENT SUPPORT

This invention was made with Government support under Grant No. BCS1445131 awarded by the National Science Foundation (NSF). The Government has certain rights in the invention.

TECHNICAL FIELD

This invention relates to a polymer-nanostructure composition for selective molecular recognition.

BACKGROUND

Molecular recognition and signal transduction are two of the main challenges in sensor design. Molecular recognition can occur when a folded and constrained heteropolymer, orientated in three dimensional space creates a binding pocket or surface that can be identified by a specific counterpart. Nature generally offers few ways to enable molecular recognition, including antibodies and aptamers. Scientists and engineers can borrow from nature to gain analyte specificity and sensitivity, using natural antibodies as vital components of the sensor. However, antibodies can be expensive, fragile, and unstable, easily losing biological activity upon modification, such as immobilization, and exhibit batch-dependent variation. These characteristics can limit their use in widespread applications. Moreover, certain molecules of interest do not have a naturally existing antibody, including toxins, drugs and explosives.

Even with a solution for molecular recognition, measuring the analyte binding event can remain a challenge. For fluorescence-based sensors, a common method has been through Förster resonance energy transfer (FRET) between acceptor and donor fluorophores; however, such sensors usually require labeling. In certain circumstances, fluorescence based sensors can utilize fluorophores that photobleach over time, significantly limiting their capability for long-term continuous monitoring. Consequently, improved systems and methods for molecular recognition and detection are needed.

SUMMARY

In general, a composition can be templated that selectively binds an analyte.

In one aspect, a composition can include a complex, wherein the complex includes a nanostructure, and a polymer, the polymer adsorbed on the nanostructure and the polymer being free from selective binding to an analyte in the absence of being adsorbed on the nanostructure, wherein the polymer is a heteropolymer including a hydrophobic region and a hydrophilic region and the polymer includes a template moiety, and a selective binding site associated with the complex, the selectivity of the selective binding site being dependent on the template moiety.

In another aspect, a sensor can include a matrix and the composition described herein suspended in the matrix.

In another aspect, a method for analyzing a sample for an analyte can include providing a composition described herein, exposing the composition to a sample, monitoring a property of the composition, and determining a presence of an analyte in the sample based on the property.

In another aspect, a system can include the composition described herein, an electromagnetic radiation source having an excitation wavelength directed at the composition, and a detector configured to receive an emission wavelength from the composition.

In another aspect, a method of making a composition can include templating a composition that selective binds an analyte. In certain circumstances, templating can include contacting a nanostructure, and a polymer, the polymer adsorbed on the nanostructure and the polymer being free from selective binding to an analyte in the absence of being adsorbed on the nanostructure, wherein the polymer is a heteropolymer including a hydrophobic region and a hydrophilic region and the polymer includes a template moiety.

In certain circumstances, the nanostructure can be a photoluminescent nanostructure. The photoluminescent nanostructure can be a nanotube, a carbon nanotube, or a single-walled carbon nanotube.

In certain circumstances, the polymer can include a polystyrene. In certain circumstances, the polymer can include a polyacrylate. In certain circumstances, the polymer can include a polyacrylate-polystyrene copolymer.

In certain circumstances, the polymer can be covalently bonded to one or more of the template moiety. In certain circumstances, the template moiety can include a steroid moiety.

In certain circumstances, the polymer can have the structure:

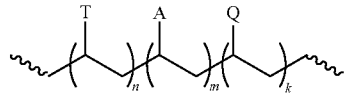

wherein n is 1 to 500, m is an integer from 0 to 500, and k is an integer from 1 to 500;

T is a template moiety;
A is a hydrophilic moiety; and
Q is a group that associates with the nanostructure.

In certain circumstances, the Q can be an aromatic group.

In certain circumstances, the template can be a cortisol, testosterone, dehydroepiandrosterone (DHEA), pregnenolone, estradiol, prednisone, corticosterone, progesterone, cortisone, aldosterone or prednisolone moiety.

In certain circumstances, the analyte is cortisol, testosterone, dehydroepiandrosterone (DHEA), pregnenolone, estradiol, prednisone, corticosterone, progesterone, cortisone, aldosterone or prednisolone.

In certain circumstances, the sample can include a gas, a liquid or a solid. In certain circumstances, the sample can be a biological fluid.

In certain circumstances, the property can be an emission, emission intensity, or an emission wavelength.

In certain circumstances, exposing the composition to a sample can include inserting the composition into an animal, a plant, or a fungus.

In certain circumstances, exposing the composition to a sample can include incubating the composition with a microorganism, a virus, a cell line, or an in vitro model system.

In certain circumstances, determining the presence of an analyte can include determining the absence of the analyte, or determining the concentration of the analyte.

In certain circumstances, monitoring a property of the composition can include creating an image.

Other aspects, embodiments, and features will be apparent from the following description, the drawings, and the claims.

BRIEF DESCRIPTION OF THE DRAWINGS

FIG. 1A shows proposed mechanism of sensor. The initial configuration of the polymer on the SWNT involves charged hydrophilic groups (blue) extending out into aqueous solution and hydrophobic monomers (orange) anchoring the polymer non-covalently onto the SWNT. A template steroid molecule (orange) is weakly bound to the SWNT, such that exogenously administered steroid molecules (magenta) will displace the appendage, resulting in a polymer configuration change and consequently change in SWNT fluorescence. FIG. 1B shows polymers were composed of hydrophobic styrene monomers and alkyl chains (orange), hydrophilic acrylic acid monomers and carboxylic acid groups (blue), and acrylated cortisol (green). FIG. 1C shows panel of steroid hormones used in the sensor screening, chosen for their physiological and therapeutic significance.

FIG. 2A shows a heat map showing the fractional fluorescence change, $(I-I_0)/I_0$, of the (9,4) and (7,6) chiralities of each member of the sensor library against 100 μM of each steroid in 2% DMSO and 1× PBS. Red denotes a fluorescence decrease, while blue indicates an increase. P indicates polymers with appendage steroids, while C denotes polymers without appendages. The full compositions of each polymer are given in Supporting Information. FIGS. 2B-2C show comparisons of composite (9,4) and (7,6) fluorescence response of HiPCO SWNT wrapped with (FIG. 2B) C2, a polymer with 0 appendage units, versus (FIG. 2C) P10, a polymer with 4 appendage units. Increasing the number of appendage units while keeping the number of acrylic acid and styrene relatively fixed at approximately 55 and 25, respectively, increased progesterone selectivity and sensitivity. FIGS. 2D-2E show a polymer with (FIG. 2D) 0 mol % styrene, P1, exhibited higher steroid sensitivity but lower selectivity compared to a polymer with (FIG. 2E) higher styrene content at 20 mol %, P13. FIG. 2F shows a UV-Vis-NIR absorption spectrum of polymer-suspended HiPCO SWNT, indicating successful suspension of SWNT in the parameter space of the polymer library.

FIG. 3A shows a cortisol sensor consists of a low styrene, high template polymer wrapped around (6,5) Comocat SWNT, whose fluorescence increases in response to cortisol. FIG. 3B shows cortisol induces approximately twice a change in fluorescence intensity magnitude versus the other steroids at the equivalent concentration of 100 μM. FIG. 3C shows a calibration curve showing sensor sensitivity from 20 μM to 100 μM. FIG. 3D shows a progesterone sensor consists of a high styrene, high template polymer wrapped around HiPCO SWNT, whose fluorescence increases in response to progesterone. FIG. 3E shows the progesterone sensor is selective towards progesterone over other steroids by a factor of 2, all tested at 100 μM. FIG. 3F shows the progesterone sensor has a detection range from 10 to 100 μM. FIG. 3G shows excitation-emission plots of the progesterone sensor showing that the (9,4) and (7,6) chiralities are most sensitive to progesterone. FIG. 3H shows the progesterone sensing mechanism is not a simple hydrophobicity sensor, indicated by its sensor response relative to its partition coefficient.

FIG. 4A shows a SWNT were encapsulated into PEGDA hydrogels, into which analytes diffuse and modulate fluorescence intensity. FIG. 4B shows a fluorescence spectrum of the progesterone sensor in 1× PBS and other commonly used hydrogel polymers before crosslinking. The degree of polymer interaction with SWNT can be seen by the shifting fluorescence spectrum. Among the different hydrogel components, PEG perturbed the sensor baseline fluorescence the least. FIG. 4C shows sensor response to 100 μM when also incubated with hydrogel materials. Of the polymers tested, PEG and poly(vinyl pyrrolidone) preserved the sensor response compared to PBS. FIG. 4D shows a progesterone sensor encapsulated in PEGDA hydrogel exposed to varying cycles of 0 (red arrows) and 100 μM (green arrows) progesterone, showing a stable and reversible response of 18%. FIG. 4E shows a calibration curve of the progesterone sensor hydrogel. FIG. 4F shows the progesterone sensor hydrogel is functional in 10% mouse serum. FIG. 4G shows excitation-emission plots show that the (9,4) and (7,6) chiralities are most sensitive to progesterone. FIG. 5A shows a response of sensor hydrogels to 100 μM progesterone outside of mice. The hydrogels were implanted subcutaneously either directly or inside of 6-8 kDa dialysis bags for varying durations of time and subsequently extracted. Direct implantation leads to deactivation over time, while the use of a dialysis bag slows the deactivation. FIG. 5B shows an FTIR spectra do not show any changes in chemical functionalities of the bulk hydrogel material with implantation time. FIG. 5C shows response of hydrogel inside of dialysis bags to 100 μM progesterone. FIG. 5D shows hydrogels inserted into 6-8 kDa dialysis bags (scale=5 mm). FIG. 5E shows two hydrogels inside of dialysis bags implanted simultaneously in the dorsal subcutaneous space of SKH1-E mice (scale=10 mm). One dialysis bag was incubated in 100 μm progesterone, while the other was incubated in the control buffer. FIG. 5F shows the dialysis bag incubated in progesterone shows a more intense fluorescence decrease over the control bag, as progesterone diffuses outside of the sensor hydrogel. FIG. 5G shows the trend was reproducible in 3 mice, with $p<0.02$.

DETAILED DESCRIPTION

Figure 1A:
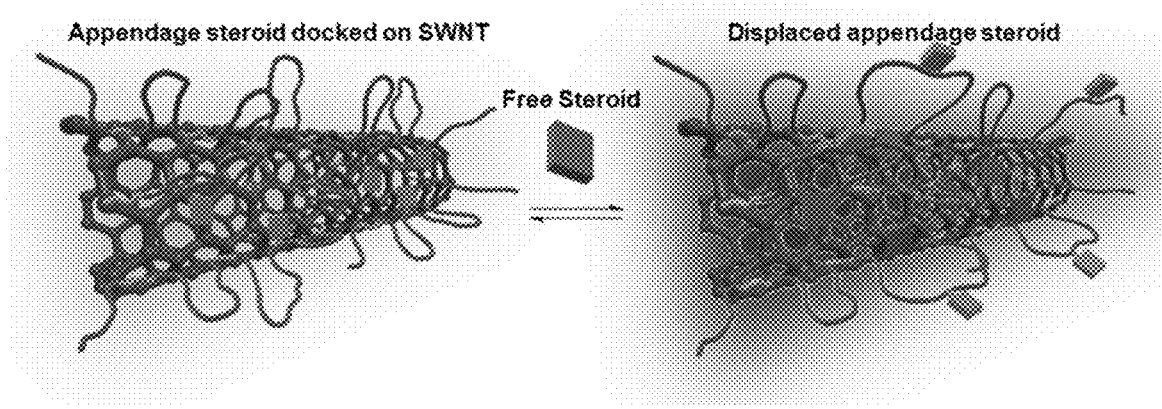
FIGS. 1A-1C depicts semi-rational design for Corona Phase Molecular Recognition sensor for steroid hormone sensing.

The invention can be an implantable near infrared fluorescent biosensor for in vivo measurements of steroid hormones, including cortisol and progesterone. The intensity and wavelength of the fluorescence changes in a concentration-dependent manner to steroids in the vicinity of the sensor. The sensor consists of several components: (1) near infrared fluorescent single walled carbon nanotubes (SWNT), (2) polymers synthesized from acrylic acid derivatives, styrene derivatives, and steroid derivatives, and (3) a biocompatible hydrogel matrix encapsulating the nanoparticles. The polymers form a corona around the carbon nanotubes, forming a barrier such that these nanoparticles interact selectively with steroids. These nanoparticles are further encased in a hydrogel such that they can be implanted into living organisms. Steroids penetrate the hydrogel and interact with the nanoparticles in a reversible manner.

Steroid signaling pathways control critical aspects of human physiology, including cortisol for the stress response, progesterone for female fertility, and testosterone for androgenic traits. Steroid hormones are also implicated in a broad array of medical conditions and pathologies, including cortisol in Cushing's disease and mental illnesses and aldosterone for adrenal cancer and irregular blood pressure. Real time, dynamic measurements of these important analytes in vivo may significantly deepen our understanding of steroid biochemistry, leading to new diagnoses and therapeutic approaches, but these measurements are limited by the availability of specific molecular recognition sites for sensor development. In this work, we apply a synthetic approach of Corona Phase Molecular Recognition (CoPhMoRE) to generate near infrared fluorescent sensors for progesterone and cortisol based on selection from a styrene and acrylic acid copolymer library augmented with an acrylated steroid, shown to self-template the corona phase as a novel CoPhMoRE strategy. Sensors exhibit excellent stability in sensor response from 1 to 200 µM with reversibility upon repeated analyte cycling, yielding KD values of 100 for progesterone. We show that molecular recognition is possible in vivo after sensor implantation into a murine model by employing a poly(ethylene glycol) diacrylate (PEGDA) hydrogel and porous cellulose interface to limit non-specific absorption. The results demonstrate that synthetic molecular recognition strategies such as CoPhMoRe are sufficiently robust to enable a new class of continuous, in vivo biosensors for insight into steroid signaling, enable new diagnostic and therapeutic approaches.

The raw SWNT were purchased from NanoIntegris and used without further purification. The acrylic acid, styrene, and steroids were purchased from Sigma. The steroid derivatives were produced by reacting cortisol and commercially available acryloyl chloride. The acrylic acid, styrene, and steroid derivative were used to produced polymers via RAFT polymerization to a final polymer with an average molar mass of 8 kDa and a final composition of roughly 67.5 mol % acrylic acid, 27.5 mol % styrene, and 5% acrylated cortisol. The polymers are combined with the SWNT in a 10:1 mass ratio, sonicated in 1× PBS at pH 7.4, and centrifuged to remove impurities. Nanoparticles are produced as a result of this process, with the polymers forming a corona around the carbon nanotubes, forming a barrier such that these nanoparticles interact selectively with steroids. The selectivity is based on the use of the steroid derivatives forming a template binding site on the surface of the SWNT in the shape of the target steroid analytes, as the polymer wraps around the SWNT.

These nanoparticles are further encased in a poly(ethylene glycol) diacrylate (PEGDA) hydrogel such that they can be implanted into living organisms. The poly(ethylene glycol) is purchased from Sigma, mixed with the nanoparticles, and cross-linked in a photopolymerization process. The components are mixed in the following proportions: PEGDA at 100-250 mg/mL and nanoparticles at 1-100 mg/L. The resulting hydrogel has a thickness of 0.5-3 mm, and the length and width are cut to size before use. The hydrogels are implanted in animals in various locations, including the subcutaneous space, the intramuscular space, inside the body cavity, or in other organs. Steroids penetrate the hydrogel and interact with the nanoparticles in a reversible manner. In this interaction, the fluorescence of the SWNT increases or decreases according to the concentration of the steroids.

The invention has several advantages. Because they are made from synthetic materials, these sensors offer higher thermal and chemical stability relative to other typically used biological materials, such as antibodies or aptamers. Antibodies and aptamers often face limited lifetimes in vivo due to their tendency to be chemically degraded. Furthermore, the single walled carbon nanotubes' near infrared fluorescence penetrates tissue more deeply compared to other commonly used organic fluorophores, allowing deeper tissues to be probed. Additionally, compared to organic fluorophores, the carbon nanotubes do not photobleach, extending the lifetime of the sensors indefinitely. The invention is the first nanosensor to be used in vivo in the literature.

With further development, there is commercial potential. Cortisol is the primary stress hormone that has erratic dynamics and is a key molecule in numerous diseases, including autoimmune disease, mental illness, and cancer. Progesterone is a primary female sex hormone at the basis of numerous diseases, including breast cancer. Our sensors offer the ability to measure continuously with high temporal resolution. Measurements of these molecules are of tremendous interest to both scientific and medical communities for research, diagnostic, and therapeutic purposes. As such, our sensors could see wide commercial viability in a wide range of customers, including laboratories, hospitals, and consumers.

A polymer, with little or no affinity for the target analyte, can adopt a specific conformation when adsorbed to a nanostructure via non-covalent interactions. In this approach, the polymer can be pinned in place such that a selective binding site can be created that recognizes the target molecule, and the binding event can lead to changes in the photoluminescence emitted. The polymer-nanotube composition can act as a binding partner for the analyte, which results in a detectable change in photoluminescence. No labeling is needed in this technique; however, labeling can be performed. For example, one or more fluorescent dyes can be conjugated to the polymer through covalent reaction with a functionality along the polymer backbone or at a polymer terminus.

A systematic design of polymers for understanding molecular structures of polymers that are capable of complexing or interacting with a nanostructure can include adjusting the hydrophilic and hydrophobic regions of the polymer forming a heteropolymer. Corona Phase Molecular Recognition (CoPhMoRe) is a generic molecular recognition scheme using a nanoparticle surface to template a heteropolymer. An adsorbed phase of a surfactant or a polymer on a nanoparticle, called the corona, and normally selected from a library of such molecules, is necessarily constrained and structured by the molecular interactions with the nanoparticle surface. CoPhMoRe is achieved when a heteropolymer—nanoparticle hybrid selectively binds a target analyte owing to the structure adopted by the polymer when folded onto the particle surface. In practice, a CoPhMoRe screen of a heteropolymer or surfactant library is accelerated if the underlying nanoparticle has an optical response to the molecular binding event, allowing for high throughput detection of the selective phase.

The heteropolymer includes one or more template moieties. The template moieties can be covalently bonded to the heteropolymer. The template moieties can influence the formation of the heteropolymer-nanoparticle hybrid such that the hybrid has an affinity for a class of analytes having a similar chemical structure to the template.

The heteropolymer-nanoparticle hybrid can have a sensitivity for an analyte such that the, when the analyte is present, the emissive properties of the hybrid are changed. The emission can be in the infrared or near-infrared wavelength range.

A sensor can be formed from the templated heteropolymer-nanoparticle hybrid. The sensor can include a matrix suspending one or more of the templated heteropolymer-nanoparticle hybrid. The matrix can be a hydrogel.

Steroid hormones are essential components in numerous metabolic pathways dictating macromolecule metabolism, homeostasis, reproduction, inflammation, among many others. See, for example, Litwack, G. in *Human Biochemistry* (ed. Litwack, G. B. T.-H. B.) 467-506 (Academic Press, 2018). doi:https://doi.org/10.1016/B978-0-12-383864-3.00016-8, which is incorporated by reference in its entirety. Consequently, dysfunction in the synthesis, signaling pathways, and degradation of these molecules are key mechanisms by which various diseases act. See, for example, Honour, J. W. Diagnosis of Diseases of Steroid Hormone Production, Metabolism and Action. *J. Clin. Res. Pediatr. Endocrinol.* 1, 209-226 (2009), which is incorporated by reference in its entirety. Steroid hormone levels are often measured as biomarkers for these diseases, though the exact biochemical mechanisms remain a central focus of basic research. Furthermore, steroids are regularly administered as therapeutics, requiring specific dosage amounts and timing based on individual patient characteristics. In vivo sensors capable of providing real-time information on steroid levels could enable faster, more accurate medical diagnoses, elucidate biochemical mechanisms of disease, and enhance therapeutic interventions through real-time feedback on efficacy. To address this problem, we have synthesized new Corona Phase Molecular Recognition sensors for steroids from initial design to an in vivo demonstration.

As regulators of gene expression, steroids control a number of processes dictating physiological and pathological mechanisms in the human body. Steroids exist in the blood between 0-500 nM, with roughly 90% of the steroids being bound to carrier proteins such as corticosteroid binding globulin (transcortin), sex-binding globulin, and serum albumin. Free steroids passively diffuse from the circulation into the interstitial spaces and eventually the intracellular space, where they bind to their receptors and act as transcription factors. See, for example, Litwack, G. in *Human Biochemistry* (ed. Litwack, G. B. T.-H. B.) 467-506 (Academic Press, 2018). doi:https://doi.org/10.1016/B978-0-12-383864-3.00016-8, Lee, M. A., Bakh, N., Bisker, G., Brown, E. N. & Strano, M. S. A Pharmacokinetic Model of a Tissue Implantable Cortisol Sensor. *Adv. Healthc. Mater.* 5, 3004-3015 (2016), Iqbal, M. J., Dalton, M. & Sawers, R. S. Binding of Testosterone and Oestradiol to Sex Hormone Binding Globulin, Human Serum Albumin and other Plasma Proteins: Evidence for Non-Specific Binding of Oestradiol to Sex Hormone Binding Globulin. *Clin. Sci.* 64, 307 LP-314 (1983) and Dorin, R. I. et al. Validation of a simple method of estimating plasma free cortisol: Role of cortisol binding to albumin. *Clin. Biochem.* 42, 64-71 (2009), each of which is incorporated by reference in its entirety. In these compartments, steroids typically exist at 0-50 nM. See, for example, Lee, M. A., Bakh, N., Bisker, G., Brown, E. N. & Strano, M. S. A Pharmacokinetic Model of a Tissue Implantable Cortisol Sensor. *Adv. Healthc. Mater.* 5, 3004-3015 (2016), which is incorporated by reference in its entirety. Steroids may also induce non-genomic effects by interaction with membrane proteins. See, for example, Falkenstein, E., Tillmann, H. C., Christ, M., Feuring, M. & Wehling, M. Multiple actions of steroid hormones—a focus on rapid, nongenomic effects. *Pharmacol. Rev.* 52, 513-556 (2000).

Among the most important steroids include cortisol and progesterone. Cortisol is the primary stress hormone that plays a key role in the stress response, macromolecular metabolism, and inflammation. See, for example, Lee, M. A., Bakh, N., Bisker, G., Brown, E. N. & Strano, M. S. A Pharmacokinetic Model of a Tissue Implantable Cortisol Sensor. *Adv. Healthc. Mater.* 5, 3004-3015 (2016), which is incorporated by reference in its entirety. Cortisol is a key marker for various diseases, including Cushing's syndrome, Addison's disease, and various types of cancers. See, for example, Gupta, S. K. & Dubé, M. P. Exogenous cushing syndrome mimicking human immunodeficiency virus lipodystrophy. *Clin. Infect. Dis.* 35, E69-71 (2002) and Napier, C. & Pearce, S. H. S. Current and emerging therapies for Addison's disease. *Curr. Opin. Endocrinol. Diabetes Obes.* 21, 147-153 (2014), each of which is incorporated by reference in its entirety. Furthermore, cortisol has been studied as a possible biomarker for neuropsychiatric diseases, including major depression, post-traumatic stress disorder, and bipolar disorder. See, for example, LeMoult, J. & Joormann, J. Depressive rumination alters cortisol decline in Major Depressive Disorder. *Biol. Psychol.* 100, 50-55 (2014), Yahyavi, S. T., Zarghami, M., Naghshvar, F. & Danesh, A. Relationship of cortisol, norepinephrine, and epinephrine levels with war-induced posttraumatic stress disorder in fathers and their offspring . *Revista Brasileira de Psiquiatria* 37, 93-98 (2015), and, Steen, N. E. et al. Altered systemic cortisol metabolism in bipolar disorder and schizophrenia spectrum disorders. *J. Psychiatr. Res.* 52, 57-62 (2014), each of which is incorporated by reference in its entirety. The World Health Organization reports that approximately 300 million people worldwide suffered from depression in 2015. See, for example, World Health Organization. Depression and other common mental disorders: global health estimates. *World Heal. Organ.* (2017). doi:CC BY-NC-SA 3.0 IGO, which is incorporated by reference in its entirety. Progesterone dictates processes regarding female sexual traits, including differentiation, fertility, menstruation, and pregnancy. See, for example, Bouchard, P. Progesterone and the progesterone receptor. *J. Reprod. Med.* 44, 153-157 (1999), which is incorporated by reference in its entirety. The dysregulation of progesterone signaling pathways delineates certain classes of female cancers, including breast cancer. See, for example, Dinny Graham, J. & Clarke, C. L. Physiological action of progesterone in target tissues. *Endocrine Reviews* (1997). doi:10.1210/er.18.4.502, which is incorporated by reference in its entirety. These diseases are both deadly and widespread, occurring in approximately 1 in 8 women with a mortality rate of 40,000 per year. See, for example, Siegel, R. L., Miller, K. D. & Jemal, A. Cancer statistics, 2018. *CA. Cancer J. Clin.* (2018). doi:10.3322/caac.21442, which is incorporated by reference in its entirety.

Measurements of steroids are key in the treatment of these diseases and others. Initial diagnosis involves the identification of aberrant steroid levels. Subsequent measurements determine the efficacy and dictate further course of treatment. For example, immunotherapies have emerged as promising candidates for the treatment of various types of cancer. However, the administration of such drugs may cause undesired immune-related adverse events (IRAEs), such as hepatitis, auto-immune diabetes, and hypothyroidism, which are subsequently treated by anti-inflammatory glucocorticoids. The glucocorticoids are typically administered over several weeks, with the dosages adjusted over time to account for individual patient traits and the stage of therapy. However, a balance exists between tempering the immune response enough to resolve the IRAEs but not excessively such that the immunotherapy becomes ineffective. To account for tumor and patient heterogeneity, this balance requires quantitative feedback with high temporal resolution, motivating the use of an in vivo sensor in order to manipulate dosages as needed.

In another example, patients with adrenal insufficiency consume glucocorticoid replacement drugs multiple times daily, with each dose being slightly different to account for the natural diurnal pattern of cortisol. Over-replacement and under-replacement are possible outcomes of erroneous dosages, resulting in undesired conditions such as exogenous Cushing's syndrome. Glucocorticoids are also used to treat osteoarthritis, various autoimmune diseases such as ulcerative colitis, and other inflammatory disorders. Additionally, steroids other than glucocorticoids are being investigated for their therapeutic potential, including sex hormones for lung diseases, Alzheimer's disease, and female cancers.

Clearly, smarter drug delivery schemes, in which dosage timing and size are controlled by existing levels of steroids in the body and consider the patients themselves, require real-time in vivo sensors continuously querying and reporting the levels of biomarkers. The current standard of measurement involves sampling blood and using chromatography or immunoassays. See, for example, Gatti, R. et al. Cortisol assays and diagnostic laboratory procedures in human biological fluids. *Clin. Biochem.* 42, 1205-1217 (2009), which is incorporated by reference in its entirety. However, these methods are too labor-intensive, costly, and lack the temporal resolution for real-time feedback. See, for example, Kaushik, A., Vasudev, A., Arya, S. K., Khalid, S. & Bhansali, S. Biosensors and Bioelectronics Recent advances in cortisol sensing technologies for point-of-care application. 53, 499-512 (2014), which is incorporated by reference in its entirety. Furthermore, in the case of cortisol, endogenous production involve a diurnal pattern, as well as stochastic release, such that single measurements fail to capture the complete profile. See, for example, Lee, M. A., Bakh, N., Bisker, G., Brown, E. N. & Strano, M. S. A Pharmacokinetic Model of a Tissue Implantable Cortisol Sensor. *Adv. Healthc. Mater.* 5, 3004-3015 (2016), which is incorporated by reference in its entirety.

New technologies for point-of-care steroids have been developed extensively. We point readers to excellent reviews regarding sensors based on molecular imprinting, aptamers, and antibodies. While point-of-care sensors have their utility in a number of important medical applications, the lack of direct access to the in vivo environment represents significant delay time and inconvenience to the patient. Such configurational weaknesses reduce the temporal resolution of the measurements and may also adversely affect patient compliance with the measurement protocols.

Conversely, in the literature, there exist only a few examples of true in vivo steroid/steroid derivative sensors, which have direct access to biological fluids through either an injection or implantation. Takase et al. coupled cholesterol oxidase and an implantable electrode to monitor the cholesterol level in eye interstitial fluid in fish for 48 hours. Cook measured cortisol in sheep and cattle using an electrochemical immunosensor implanted into the jugular veins. Cook also used a microdialysis probe coupled to an immunosensor implanted in the amygdala of sheep to measure cortisol.

In vivo steroid detection remains a challenging problem, but Corona Phase Molecular Recognition (CoPhMoRe) has emerged as a promising solution to create implantable nanosensors capable of in vivo measurements. In this technique, non-biological antibodies are created by non-covalently dispersing fluorescent single walled carbon nanotubes (SWNT) with polymers, whose configuration on the nanoparticle excludes most molecules from interacting with the SWNT. Signal transduction is built into the nanoparticle as changes in the SWNT fluorescence spectrum. SWNT are particularly advantageous for long-term, spatiotemporal monitoring because they fluoresce in the tissue transparency window and do not have photobleaching. See, for example, Iverson, N. M. et al. In vivo biosensing via tissue-localizable near-infrared-fluorescent single-walled carbon nanotubes. *Nat. Nanotechnol.* 8, 873-880 (2013), which is incorporated by reference in its entirety. Furthermore, the selectivity of the sensors can be tuned by modifying the suspending polymer. Previous CoPhMoRe sensors have included dopamine, riboflavin, L-thryoxine, estradiol, nitric oxide, fibrinogen, and insulin. See, for example, Kruss, S. et al. Neurotransmitter detection using corona phase molecular recognition on fluorescent single-walled carbon nanotube sensors. *J. Am. Chem. Soc.* 136, 713-724 (2014), Kruss, S. et al. High-resolution imaging of cellular dopamine efflux using a fluorescent nanosensor array. *Proc. Natl. Acad. Sci.* 114, 1789-1794 (2017), Zhang, J. et al. Molecular recognition using corona phase complexes made of synthetic polymers adsorbed on carbon nanotubes. *Nat. Nanotechnol.* 8, 959-68 (2013), Zhang, J. Q. et al. Single Molecule Detection of Nitric Oxide Enabled by d(AT)(15) DNA Adsorbed to Near Infrared Fluorescent Single-Walled Carbon Nanotubes. *J. Am. Chem. Soc.* 133, 567-581 (2011), Giraldo, J. P. et al. A Ratiometric Sensor Using Single Chirality Near-Infrared Fluorescent Carbon Nanotubes: Application to in Vivo Monitoring. *Small* 11, 3973-3984 (2015), Bisker, G. et al. Protein-targeted corona phase molecular recognition. *Nat. Commun.* 7, (2016), and Bisker, G. et al. Insulin Detection Using a Corona Phase Molecular Recognition Site on Single-Walled Carbon Nanotubes. *ACS Sensors* 3, 367-377 (2018), each of which is incorporated by reference in its entirety. The nitric oxide sensor has been used in vivo and shown to maintain its fluorescence stability over 400 days. See, for example, Iverson, N. M. et al. In vivo biosensing via tissue-localizable near-infrared-fluorescent single-walled carbon nanotubes. *Nat. Nanotechnol.* 8, 873-880 (2013), which is incorporated by reference in its entirety.

CoPhMoRe has shown its versatility in the recognition of various classes of molecules with remarkable structural diversity, which make the technique an appealing choice for a steroid sensor. Some questions remain, however. While there have been some efforts to establish design principles between polymer dispersant structure and corresponding CoPhMoRe sensor structure, to date, CoPhMoRe sensors have been discovered empirically, utilizing dispersants known to suspend SWNT well but not with a clear structural correlate to the target analyte. See, for example, Bisker, G. et al. A mathematical formulation and solution of the CoPhMoRe inverse problem for helically wrapping polymer corona phases on cylindrical substrates. *J. Phys. Chem. C* 119, 13876-13886 (2015), Salem, D. P. et al. Chirality dependent corona phase molecular recognition of DNA-wrapped carbon nanotubes. *Carbon N. Y.* 97, 147-153 (2016), and Salem, D. P. et al. Ionic Strength-Mediated Phase Transitions of Surface-Adsorbed DNA on Single-Walled Carbon Nanotubes. *J. Am. Chem. Soc.* 139, 16791-16802 (2017), each of which is incorporated by reference in its entirety. Furthermore, while CoPhMoRe has been shown to differentiate between molecules with wildly different structures, it has not yet been used within a class of molecules that have only slight variations on a structural motif. Last, a CoPhMoRe sensor based on synthetic polymers has not yet been taken from the first step of design to the end of an in vivo demonstration. This work addresses all of these questions.

Novel CoPhMoRe sensors for steroids were fabricated by non-covalently functionalizing SWNT with polymers incorporating template steroid molecules in a semi-rational manner. Compositional variants of the styrene, acrylic acid, template steroid polymers were synthesized, coupled to SWNT, and screened against a panel of steroid hormone chosen for their physiological and/or therapeutic significance. Selective fluorescent responses were found for cortisol and progesterone. The progesterone sensor was encapsulated into a poly(ethylene glycol) diacrylate (PEGDA) hydrogel which was formulated to optimize sensitivity and binding kinetics. The sensor hydrogels were found to be deactivated when directly implanted subcutaneously into mice, so they were further encapsulated into dialysis bags. This configuration allowed the sensors to respond to local progesterone levels while in the subcutaneous space of the mouse.

Near infrared (nIR) fluorescent single walled carbon nanotubes (SWCNT) can be used as an underlying reporter of this molecular interaction, where non-covalent functionalization was used to produce distinct corona phases. See, Bisker, G., Iverson, N. M., Ahn, J. & Strano, M. S. A Pharmacokinetic Model of a Tissue Implantable Insulin Sensor. *Advanced Healthcare Materials* 4, 87-97 (2015), Mu, B. et al. Recent Advances in Molecular Recognition Based on Nanoengineered Platforms. *Accounts of Chemical Research,* doi: 10.1021/ar400162w (2014), Kruss, S. et al. Carbon nanotubes as optical biomedical sensors. *Advanced Drug Delivery Reviews* 65, 1933-1950 (2013), Landry, M. et al. Experimental Tools to Study Molecular Recognition within the Nanoparticle Corona. *Sensors* 14, 16196-16211 (2014), Iverson, N. M. et al. In vivo biosensing via tissue-localizable near-infrared-fluorescent single-walled carbon nanotubes. *Nat Nano* 8, 873-880, doi:10.1038/nnano.2013.222 (2013), Zhang, J. et al. Molecular recognition using corona phase complexes made of synthetic polymers adsorbed on carbon nanotubes. *Nat Nano* 8, 959-968 (2013), Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), Welsher, K. et al. A route to brightly fluorescent carbon nanotubes for near-infrared imaging in mice. *Nat Nano* 4, 773-780 (2009), Giraldo, J. P. et al. A Ratiometric Sensor Using Single Chirality Near-Infrared Fluorescent Carbon Nanotubes: Application to In Vivo Monitoring. *Small,* doi:10.1002/smll.201403276 (2015), and Oliveira, S. F. et al. Protein Functionalized Carbon Nanomaterials for Biomedical Applications. *Carbon* 95, 767-779 (2015), each of which is incorporated by reference in its entirety.

CoPhMoRe screening for small molecules normally proceeds with the construction of a heteropolymer library such that each element can suspend the nanoparticle (SWCNT in this case) creating an array of colloidal dispersions. See, Zhang, J. et al. Molecular recognition using corona phase complexes made of synthetic polymers adsorbed on carbon nanotubes. *Nat Nano* 8, 959-968 (2013), and Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), each of which is incorporated by reference in its entirety. The specific synthetic polymers for library screening necessarily have hydrophobic segments or moieties that adsorb onto the hydrophobic surface of the SWCNT, pushing hydrophilic segments into solution. The composition of the polymer controls the specific configuration, either static or dynamic, that can recognize a target analyte of interest. For small molecules, the interaction between the polymer, nanotube and analyte can be described using a 2D Equation of State model, allowing reasonably accurate prediction of molecular recognition. See, Ulissi, Z. W., Zhang, J., Sresht, V., Blankschtein, D. & Strano, M. S. 2D Equation-of-State Model for Corona Phase Molecular Recognition on Single-Walled Carbon Nanotube and Graphene Surfaces. *Langmuir* 31, 628-636 (2014), which is incorporated by reference in its entirety. In the case of SWCNT, high throughput fluorescence spectroscopy that scans for spectral changes associated with analyte binding as either fluorescent intensity or emission wavelength modulation can then be used to identify CoPhMoRe phases. Previous work has demonstrated CoPhMoRe SWCNT sensors for riboflavin, L-thyroxine, and estradiol, utilizing boronic acid-substituted phenoxy-dextran, polyethylene glycol (PEG) brush, and rhodamine isothiocyanate (RITC) difunctionalized-PEG SWCNT coronae, respectively. See, Zhang, J. et al. Molecular recognition using corona phase complexes made of synthetic polymers adsorbed on carbon nanotubes. *Nat Nano* 8, 959-968 (2013), which is incorporated by reference in its entirety. Additionally, a variety of DNA oligonucleotides demonstrated discrimination among a panel of neurotransmitters. See, Kruss, S. et al. Neurotransmitter Detection Using Corona Phase Molecular Recognition on Fluorescent Single-Walled Carbon Nanotube Sensors. *Journal of the American Chemical Society* 136, 713-724 (2013), which is incorporated by reference in its entirety. Despite initial success with small organic molecules detection, CoPhMoRe has not yet been adapted or demonstrated for macromolecules, with an open question of whether such coronae are capable of the large area, selective interactions necessary to discriminate between soluble proteins.

Although antibodies can be raised to identify both small and macro-molecular targets alike, the need of a living organism for production poses a limitation in high throughput exploratory research. See, Jayasena, S. D. Aptamers: An Emerging Class of Molecules That Rival Antibodies in Diagnostics. *Clinical Chemistry* 45, 1628-1650 (1999), which incorporated by reference in its entirety. In principle, a pinned configuration of a specific polymer could be found such that it maps the contours and localized chemical affinities of a certain face of a protein analyte (see. Bisker, G. et al. A Mathematical Formulation and Solution of the CoPhMoRe Inverse Problem for Helically Wrapping Polymer Corona Phases on Cylindrical Substrates. *The Journal of Physical Chemistry C* 119, 13876-13886 (2015). which is incorporated by reference in its entirety), but experimental realization of this has not yet been demonstrated. As a synthetic approach for recognizing these biological molecules, it is possible that protein CoPhMoRe would find extensive use in a variety of sensor and assay arrangements where degradation, stability, cost, and production scale prevent natural recognition elements from being employed.

Each of the fluorescent moiety and the polymer backbone moiety can be selected to have a length of a hydrophilic region and length of a hydrophobic region configured to interact in with a nanostructure. Selecting can include adjusting the length of the polymer moiety. Therefore, in addition to interacting with an analyte, the systemically designed polymer can suspend a nanoparticle in an aqueous solution. The length and hydrophilicity of the hydrophilic regions can be altered to achieve the desired solubility. For example, the molecular weight of a PEG conjugate can be increased or decreased to alter the solubility of composition including the polymer and a nanoparticle. In another example, a conjugate of the polymer with another moiety can be formed. The other moiety can be a fluorescent moiety which is coupled to a selected polymer backbone moiety. The fluorescent moiety can be photoluminescent nanostructure, for example, a carbon nanotube.

The polymer can be a copolymer. The copolymer can be a block copolymer. The copolymer can be a random copolymer. In certain circumstances, one block can be a random copolymer and another block can be a homopolymer. The block copolymer can have a first oligomer section and a second oligomer section. The first oligomer section can be a portion of the polymer that associates with the fluorescent moiety, for example, a styrene moiety. The first oligomer section is covalently bonded to the second oligomer section. The second oligomer section includes at least one template moiety. The template moiety can be conjugated to the second oligomer section. The template moiety can have a structure similar to a target analyte. For example, the template moiety can be a steroid. The polymer can include a third oligomer section. The third oligomer can have a hydrophilic group, for example, a carboxylic acid moiety.

Each of the first oligomer section, the second oligomer section, and the third oligomer section, when present, can have a degree of polymerization of between 2 and 500, between 5 and 400, between 10 and 250.

The polymer can have a structure with the following structure:

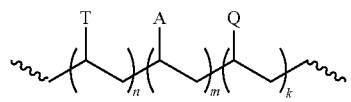

In the polymer, n can be an integer from 1 to 500, 2 to 400, 3 to 300, or 4 to 250. In certain circumstance, n can be 1 to 100. The group T can be a template moiety. The template moiety can be covalently bonded to the polymer backbone with an ester, ether, amide, carbonate, urethane, carbon-carbon bond or urea linkage. The template moiety can have a chemical structure that is analogous to an analyte. For example, the template moiety has core ring structure that is substantially similar to the analyte. The template moiety can have a steroidal ring structure and the analyte can have a steroidal ring structure. The polymer can include 1, 2, 3, 4, 5, 6, 7, 8, 9, 10, 11, 12, 13, 14, 15, 20, 30, 40, or 50 T groups.

In the polymer, m can be an integer from 0 to 500, 2 to 400, 3 to 300, or 4 to 250. In certain circumstance, m can be 1 to 250, 2 to 100, or 2 to 50. The group A can be a hydrophilic moiety. The hydrophilic moiety can include a carboxylic acid, ester, ether, amide, carbonate, urethane, sulfonyl, or urea group.

In the polymer, k can be an integer from 1 to 500, 2 to 400, 3 to 300, or 4 to 250. In certain circumstance, m can be 0 to 100. The group Q can be a group that associates with the fluorescent moiety. The group Q can be an aromatic group such as a phenyl or substituted phenyl, which can associate with a fluorescent moiety such as a carbon nanotube.

The polymer can be a polystyrene-polyacrylate copolymer including one or more template moiety.

A conjugate can be formed by reaction between one or more of a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal. Specific examples can include N-succinimidyl carbonate, amine, hydrazide, succinimidyl propionate, succinimidyl butanoate, succinimidyl succinate, succinimidyl ester, benzotriazole carbonate, glycidyl ether, oxycarbonylimidazole, p-nitrophenyl carbonate, aldehyde, maleimide, orthopyridyl-disulfide, or vinylsulfone.

In other circumstances, the polymer can be branched or modified in other ways to alter or adjust the properties of the complex. For example, the polymer can be a comb, brush or star-burst polymer. For example, the polymer can be branched, having 2-20 arms. In certain examples, the branched polymer can be a polyethylene glycol polymer having 2, 4 or 8 arm groups.

Generally, the composition can include a complex and a selective binding site associated with the complex. The complex can include a nanostructure and a polymer, the polymer being free from selective binding to an analyte in the absence of being adsorbed on the nanostructure. The polymer can be adsorbed on the nanostructure. The nanostructure can be a photoluminescent nanostructure.

A nanostructure can be an article having at least one cross-sectional dimension between opposed boundaries of less than about 1 micron. In some embodiments, nanostructures can have at least one cross-sectional dimension between opposed boundaries of less than about 500 nm, less than about 250 nm, less than about 100 nm, less than about 75 nm, less than about 50 nm, less than about 25 nm, less than about 10 nm, or, in some cases, less than about 1 nm. Examples of nanostructures can include nanotubes (including carbon nanotubes), nanowires (including carbon nanowires), graphene and quantum dots, among others. In some embodiments, the nanostructures can include a fused network of atomic rings, the atomic rings can include a plurality of double bonds.

A photoluminescent nanostructure can be a class of nanostructures that can exhibit photoluminescence. In some embodiments, photoluminescent nanostructures can exhibit fluorescence. In some instances, photoluminescent nanostructures can exhibit phosphorescence. Examples of photoluminescent nanostructures suitable for use can include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, or graphene, among others. In some embodiments, the photoluminescent nanostructures can be a semi-conductive single-walled carbon nanotube.

Selective binding can be sufficiently specific that it can be used to distinguish the analyte from other chemical species. The polymer can be considered random because, in the absence of the complex, the polymer has little or no affinity for the analyte.

In some embodiments, the polymer can be a polynucleotide. The polynucleotide can be DNA or RNA. The polynucleotide can be single stranded or double stranded. The polynucleotide can be single stranded in one section and double stranded in another section. RNA can include mRNA, siRNA or shRNA.

The polynucleotide can form a structure. Exemplary nucleic acid structures can include an A-form double helix, a B-form double helix, a Z-form double helix, a hairpin, a loop or a stem loop.

The polynucleotide can contain ribonucleotides or deoxyribonucleotides. The polynucleotide can have less than 100,000, less than 50,000, less than 25,000, less than 10,000, less than 5,000, less than 1,000, less than 500, less than 250, less than 100, less than 75, less than 50, less than 30, less than 25, less than 20, 15, 12, 10, 8, 6 or 4 nucleotides.

The polynucleotide can have a random sequence. The polynucleotide can have an ordered sequence. The ordered sequence can be a predetermined sequence. For example, an ordered sequence can be the sequence of a gene. The ordered sequence can be a repeating sequence. The repeat sequence can include less than 500, less than 400, less than 300, less than 200, less than 100, less than 50, less than 30, less than 25, less than 20, 15, 14, 13, 12, 11, 10, 9, 8, 7, 6, 5, 4, 3 or 2 nucleotides. The polynucleotide can be poly(AT), poly (GT), poly(CT), poly(AG), poly(CG), or poly(AC). The polynucleotide can have a content. The content can be a percentage of a unique nucleotide present in the sequence. The percentage can be 100% of a unique nucleotide, including poly(A), poly(C), poly(G), poly(T) or poly(U).

In some embodiments, the polymer can be a polylipid. The polylipid can include a phospholipid, a palmitoyl phospholipid or 1,2-dipalmitoyl-sn-glycero-3-phosphoethanolamine-N-(lauroyl) (PL-DOD).

In other embodiments, the polymer can be polyvinylpyrrolidone, a poly(ethylene oxide), a poly(styrene), a poly (acrylate), a poly(ethylene oxide)—poly (propylene oxide)—poly (ethylene oxide) block co-polymer, poly (N-isopropyl acrylamide), polyethyleneimine, polyacrylamide, polyvinyl alcohol or collagen.

In some embodiments, the polymer can be a polypeptide. In some embodiments, the number of amino acids comprising the polypeptide can fall within a specific range. For example, the polypeptide can include between 5 and about 50 amino acid residues, or between 5 and about 30 amino acid residues. In other embodiments, the polypeptide can fall within a specific molar mass range. For example, the polypeptide can have a molecular weight of between 400 g/mol and about 10,000 g/mol, or between 400 g/mol and about 6,000 g/mol. The polypeptide can be a protein, having greater than about 50 amino acid residues. The polypeptide can be a fragment of a protein. In some embodiments, the polypeptide can be expressed in a disease state. In other embodiments, the polypeptide can be modified. In some circumstances, the polypeptide can be modified by attaching functional groups. In other circumstances, the polypeptide can be ubiquinated, biotinylated, glycosylated, PEGylated or SUMOylated. The polypeptide can be a biomarker, an enzyme, a receptor, a ligand, a peptide hormone, a neuropeptide, a vasoactive intestinal peptide, a chaperone or an antibody.

The polypeptide can, in some instances, include a peptide sequence observed in the venom of an animal or a derivative thereof. In some cases, the polymer can include a polypeptide sequence (or derivative thereof) observed in the venom of a member of the Insecta class, the Hymenoptera order, or the Vespidae or Apidae families. In some embodiments, the polypeptide can be a member the Mastoparan or Bombolitin (including Bombolitin II, Bombolitin III) families of polypeptides, or derivatives of those polypeptides. The polypeptide can include a mastoparan, mastoparan 7 or mastoparan X.

In the complex, the polymer can be adsorbed on the photoluminescent nanostructure. While individual polymers can be adsorbed or pinned to one point on the nanotube, it should be understood that the polymer can assume any suitable shape or configuration on the nanotube.

While the polymer can be free from selective binding to the analyte, the composition can include a selective binding site associated with the complex. The selective binding site can be associated with the polymer. The selective binding site can also be associated with the nanostructure. Additionally, the selective binding site can be associated with both the polymer and the nanostructure.

Changing the ratio of the amount of polymer to the amount of photoluminescent nanostructure can result in different compositions, which can interact differently with an analyte. Changing the ratio of a first type of monomer in the polymer to a second type of monomer in the polymer also can result in different compositions. A different polymer can result in a different selective binding site. A different polymer can alter a property of the composition. The property can be an emission.

The diameter of a photoluminescent nanostructure can be different from the diameter of another photoluminescent nanostructure. The diameter of the photoluminescent nanostructure can affect the adsorbtion of the polymer on the photoluminescent nanostructure. The diameter of the photoluminescent nanostructure can affect the selective binding site. The diameter of the photoluminescent nanostructure can affect a property of the composition. The property of the composition can be an emission.

Carbon nanotubes can be classified by the chiral vector (n,m) that can characterize the orientation of the carbon hexagons in a corresponding graphene sheet. The chiral vector of a photoluminescent nanostructure can be different from the diameter of another photoluminescent nanostructure. The chiral vector of the photoluminescent nanostructure can affect the adsorbtion of the polymer on the photoluminescent nanostructure. The chiral vector of the photoluminescent nanostructure can affect the selective binding site. The chiral vector of the photoluminescent nanostructure can affect a property of the composition. The property of the composition can be an emission.

In some embodiments, the analyte can be a small molecule, protein, biomolecule, explosive, drug, biologic, or a metabolite thereof. For example, the analyte can be monosaccharide, a polysaccharide, an amino acid, a nucleotide, an oligonucleotide, a lipid, a polylipid or a steroid. More specifically, the analyte can be riboflavin or nitric oxide. In some embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramin or urea. In some embodiments, the analyte can be a DNA sequence, a RNA sequence or a siRNA sequence. In some embodiments, the analyte can be albumin, Immunoglobulin G (IgG), fibrinogen, α1-antitrypsin, transferrin, haptoglobin, α2-macroglobulin, Immunoglobulin A (IgA), Immunoglobulin M (IgM), α1-acidglycoprotein, and apoliporprotein A-I, insulin, human chorionic gonadotropin (hCG), and C-reactive protein (CRP), or any other protein present in the human blood.

In other embodiments, the analyte can be a peptide or a protein. In some embodiments, the number of amino acids comprising the polypeptide can fall within a specific range. For example, the polypeptide can include between 5 and about 50 amino acid residues, or between 5 and about 30 amino acid residues. In other embodiments, the polypeptide can fall within a specific molar mass range. For example, the polypeptide can have a molecular weight of between 400 g/mol and about 10,000 g/mol, or between 400 g/mol and about 6,000 g/mol. The polypeptide can be a protein, having greater than about 50 amino acid residues. The polypeptide can be a fragment of a protein. In some embodiments, the polypeptide can be expressed in a disease state. In other embodiments, the polypeptide can be modified. In some circumstances, the polypeptide can be modified by attaching functional groups. In other circumstances, the polypeptide can be ubiquinated, biotinylated, glycosylated, PEGylated or SUMOylated. The polypeptide can be a biomarker, an enzyme, a receptor, a ligand, a peptide hormone, a neuropeptide, a vasoactive intestinal peptide, a chaperone or an antibody.

The composition can be used for analyzing a sample for an analyte. The method for analyzing a sample for an analyte can include providing a composition which can include a complex and a selective binding site associated with the complex. The complex can include a photoluminescent nanostructure and a polymer free from selective binding to an analyte. The polymer can be adsorbed on the photoluminescent nanostructure. The method can include exposing the composition to a sample. The method can also include monitoring a property of the composition. The method can include determining the presence of an analyte in the sample based on the property.

In some embodiments, the sample can include a gas, a liquid or a solid. In other embodiments, the sample can be a biological fluid.

In some embodiments, exposing the composition to a sample can include inserting the composition into an animal. In particular, the animal can be a human. In other embodiments, exposing the composition to a sample can include inserting the composition into a plant or fungus. Inserting can include embedding the composition within the organism, embedding the composition within a cell of the organism, puncturing the organism with the composition or inserting the composition in a natural opening of the organism, among others.

Exposing the composition to a sample can also include incubating the composition with a microorganism or a virus. Exposing the composition to a sample can include incubating the composition with a cell line. In still other embodiments, exposing the composition to a sample can include incubating the composition with an in vitro model system.

In some embodiments, the property can be an emission. More specifically, the emission can be photoluminescence. The photoluminescence can be fluorescence or phosphorescence. In some embodiments, the property can be emission intensity. In other embodiments, the property can be an emission wavelength.

Monitoring the property can include observing the property of the composition alone. Monitoring the property can include monitoring the property after the composition has been exposed to the sample. Monitoring the property can include monitoring the property after the composition has been exposed to the analyte. Monitoring the property can include monitoring the property after the composition has been exposed to known concentrations of the analyte.

Monitoring a property of the composition can include observing the property through a microscope. Monitoring a property of the composition can include measuring the property using a microscope. The microscope can be a near infrared microscope. The microscope can be a dual-channel microscope. Monitoring a property of the composition can include monitoring the property using still photography or movies. The photography or movies can be on film media or digital form.

Determining the presence of an analyte can include determining the absence of the analyte. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90% pure, greater than 95% pure, greater than 99% pure or greater than 99.9% pure.

In some embodiments, the method for analyzing a sample for an analyte further includes obtaining a sample. More specifically, the method can include obtaining a sample from an animal, a microorganism, virus, plant, fungus or cell line. The animal can be a human. A sample can be obtained by drawing blood or other bodily fluids, biopsy, scraping, excision, lysis or plucking, among others.

In some embodiments, the method for analyzing a sample for an analyte includes coating a glass slide with the composition. The glass slide can be treated with a silane prior to coating with the composition. The silane can enhance adhesion of the composition to the glass slide. The silane can be 3-aminopropyltriethoxysilane (APTES).

In one aspect, a system can include a composition which can include a complex and a selective binding site associated with the complex. The complex can include a photoluminescent nanostructure and a polymer, the polymer being free from selective binding to an analyte in the absence of being adsorbed on the nanostructure. The polymer can be adsorbed on the photoluminescent nanostructure. The system can include an electromagnetic radiation source having an excitation wavelength directed at the composition. The system can include a detector configured to receive an emission wavelength from the composition.

The electromagnetic radiation source can be a light source. The electromagnetic radiation source can be a laser. The electromagnetic radiation can include radio waves, microwaves, terahertz radiation, infrared radiation, visible light, ultraviolet radiation, X-rays and gamma rays. The electromagnetic radiation can have an excitation wavelength in the visible spectrum, near infrared spectrum or infrared spectrum.

The detector can include a near infrared detector. The detector can include a near infrared fluorometer. The detector can be mounted on a microscope.

One advantage of the composition can be that for target protein or protein therapeutic detection the need to tag or label the target therapeutic to enable detection can be eliminated. One advantage of the composition can be that composition will bind directly to the analyte. Another advantage of the composition can be that the composition will work for detecting small molecules, antibodies, antibody fragments, proteins, and peptide fragments. An additional advantage of the composition can be that the composition can detect molecules for which there is no known binding partner. An advantage of the composition can be that, due to the non-photobleaching nature of SWCNT, the composition can allow for continuous detection of the target analyte.

The composition can also be used for separation techniques. The method can include providing a composition. The composition can include a complex and a selective binding site associated with the complex. The complex can include a photoluminescent nanostructure and a polymer, the polymer being free from selective binding to an analyte in the absence of being adsorbed on the nanostructure. The polymer can be adsorbed on the photoluminescent nanostructure. The method can include exposing the composition to a mixture containing the analyte. The method can include separating the composition from the mixture. Separating the composition from the mixture can remove the analyte from the mixture.

An advantage of the composition can be that the composition may be able separate molecules for which there is no known binding partner. Another advantage of the compositions may be that the composition will work for the separation of analytes, including small molecules, antibodies, antibody fragments, proteins, and peptide fragments, among others. An advantage of the composition can be that one complex may be capable of binding multiple target molecules. Binding of multiple target molecules may allow for enhanced separation. An advantage of the composition can be that the separation process can be scalable.

In some embodiments, the composition can further include an amount of the analyte. In some embodiments, the analyte is a therapeutic. The composition can be used to deliver the therapeutic. The method can include providing a composition that includes an amount of the therapeutic. The method can include administering the composition to an animal. Administering the composition can include administering the composition by topical, enteral, parenteral, transdermal, transmucosal, inhalational, intracisternal, epidural, intravaginal, intravenous, intramuscular, subcutaneous, intradermal or intravitreal administration. In some embodiments, the method can further include monitoring a property of the composition. The method can also include determining the presence of the therapeutic in the composition based on a property. The property can be an emission, an emission intensity or an emission wavelength. Determining the presence of the therapeutic can include determining the presence, the absence or the concentration of the therapeutic.

One advantage of the composition, which can include a therapeutic, can be the possibility of a multivalent interaction between the polymer—SWCNT and the drug. The possibility of a multivalent interaction may be due to multiple binding sites along the length of the nanotube. The possibility can also mean the composition drug efficacy would be higher. Another advantage of the composition can be a concentrated drug release from the composition. A concentrated drug release may be due to one nanotube potentially containing many therapeutic molecules. An advantage of the composition can be resistance of the therapeutic to enzymatic degradation in the blood. This can be because the therapeutic can be shielded or protected within the composition. Still another advantage can be the possibility of tracing the pharmacokinetic pathways. Tracing the pharmacokinetic pathways of the drug may elucidate in vivo reaction pathways and enhance further drug design. Tracing may be possible because the SWCNT NIR fluorescence is tissue transparent.

The composition can also be used in catalysis reactions. The method can include providing the composition, including an amount of the analyte. The method can include exposing the composition to a catalyst. The method can further include monitoring a property of the composition. The method can also include determining modification of the analyte based on the property.

An advantage of the composition can be the possibility to do site-specific functionalization of target proteins, antibodies, antibody fragments and peptides. Another advantage of the composition can be the possibility to do site-specific small molecule reactions. The small molecule reactions can be similar to those done in nature by enzymatic reactions.

A method for determining analytes recognized by the selective binding site in the composition can include exposing different compositions to an analyte. Two or more compositions can be different from one another because the compositions contain different polymers from one another. Two or more compositions can be different from one another because the compositions contain the same polymer of different lengths. Two or more compositions can also be different from one another because the compositions contain polymers that are comprised monomers in different ratios. Two or more compositions can be different from one another because the compositions contain the same monomers but in one polymer the monomers are modified. Two or more compositions can be different from one another because the compositions contain different photoluminescent nanostructures. Two or more compositions can be different from one another because the compositions contain photoluminescent nanostructures of different diameters. Two or more compositions can be different from one another because the compositions contain photoluminescent nanostructures with different chiral vectors.

A method for determining analytes recognized by the selective binding site in the composition can include exposing different analytes to a composition.

A method for determining analytes recognized by the selective binding site in the composition can include monitoring a property of the composition. The property can be an emission, emission intensity or emission wavelength. Monitoring the property can include observing the property of the composition alone. Monitoring the property can include monitoring the property after the composition has been exposed to a sample. Monitoring the property can include monitoring the property after the composition has been exposed to the analyte. Monitoring the property can include monitoring the property after the composition has been exposed to known concentrations of the analyte. Monitoring the property of the composition can provide a data set associated with an analyte.

The data set can include the emission of the photoluminescent nanostructure. The data set can include a change in emission intensity observed between a first emission intensity in the presence of the analyte and a second emission intensity in the absence of the analyte. The data set can include a change in emission wavelength shift observed between an emission wavelength in the presence of the analyte and an emission wavelength in the absence of the analyte. The data set can include data obtained from applying algorithms to the data obtained by monitoring the property. The data set can include binding constants. The data set can be used to determine if the composition can selectively bind to the analyte. The data set can be used to determine if the composition binding to the analyte can be detected by monitoring a property of the composition.

A method for determining analytes recognized by the selective binding site in the composition can be a high-throughput screening assay. A method for analyzing samples in a high-throughput system can include providing an array including a plurality of compositions, exposing each composition to at least one sample, monitoring a property of each composition, and determining a presence of an analyte in the sample based on the property. Each composition in the array can include a complex, where the complex can include a nanostructure, and a polymer. The polymer can be adsorbed on the nanostructure and the polymer can be free from selective binding to an analyte in the absence of being adsorbed on the nanostructure. A selective binding site can be associated with the complex.

A well plate array can be used for exposing the composition to an analyte. The composition in different individual wells can include different individual polymers. The composition in different individual wells can include the same polymer. In some embodiments, the composition in different individual wells can be exposed to different individual analytes. In other embodiments, the composition in different individual wells can be exposed to the same analyte.

It can be determined using the methods above that a specific composition can selectively bind to a specific analyte. The specific composition can be used for detecting the analyte in a sample. The specific composition can detect the specific analyte in a sample containing other analytes. The specific composition can be mixed with other compositions. The other compositions can have selective binding for other analytes. The specific composition mixed with other compositions can detect the specific analyte in a sample. The specific composition mixed with other compositions can detect the specific analyte in a sample containing other analytes. In addition, more than one specific composition mixed with other compositions can detect the specific analytes corresponding to the specific analytes in a sample containing other analytes.

For example, composition A can detect analyte A; composition B can detect analyte B; and composition C can detect analyte C. It is possible that composition A can detect analyte A in a mixture including analyte A, analyte B, and analyte C. Furthermore, it is possible that composition A, in a mixture including composition A, composition B and composition C, can detect analyte A. Additionally, it is possible that composition A, in a mixture including composition A, composition B and composition C, can detect analyte A from a sample including analyte A, analyte B and analyte C. The analyte can be one of the steroids depicted in FIG. 1C.

Results and Discussion

Rationale for Polymer Library Design. Central to the synthetic strategy of the Corona Phase Molecular Recognition (CoPhMoRe) technique (FIG. 1A) is a polymer adsorbed and pinned into a configuration onto a nanoparticle surface, which also acts as a sensor transducer for the reporting of molecular binding. See, for example, Kruss, S. et al. Neurotransmitter detection using corona phase molecular recognition on fluorescent single-walled carbon nanotube sensors. *J. Am. Chem. Soc.* 136, 713-724 (2014), Zhang, J. et al. Molecular recognition using corona phase complexes made of synthetic polymers adsorbed on carbon nanotubes. *Nat. Nanotechnol.* 8, 959-68 (2013), Bisker, G. et al. Protein-targeted corona phase molecular recognition. *Nat. Commun.* 7, (2016) and Bisker, G. et al. Insulin Detection Using a Corona Phase Molecular Recognition Site on Single-Walled Carbon Nanotubes. ACS Sensors 3, 367-377 (2018), each of which is incorporated by reference in its entirety. Computational models can be used to predict the underlying corona phase structures and necessary binding constants for robust functioning in in vivo environments. See, for example, Lee, M. A., Bakh, N., Bisker, G., Brown, E. N. & Strano, M. S. A Pharmacokinetic Model of a Tissue Implantable Cortisol Sensor. *Adv. Healthc. Mater.* 5, 3004-3015 (2016), Bisker, G. et al. A mathematical formulation and solution of the CoPhMoRe inverse problem for helically wrapping polymer corona phases on cylindrical substrates. *J. Phys. Chem. C* 119, 13876-13886 (2015) and Bisker, G., Iverson, N. M., Ahn, J. & Strano, M. S. A Pharmacokinetic Model of a Tissue Implantable Insulin Sensor. *Adv. Healthc. Mater.* 4, 87-97 (2015), each of which is incorporated by reference in its entirety. In this work, we explore a synthetic approach whereby a chemical appendage off of the backbone of the polymer, similar in molecular weight and chemical structure to the target analyte (FIG. 1b), creates a reversible binding pocket within the corona phase. The rationale is that as the polymer adsorbs and becomes the nanoparticle corona, the appendage self-templates the corona, creating an encapsulating binding pocket ideal for analyte recognition. We hypothesize that the appendage should reversibly adsorb, while still attached to the backbone, such that the vacancy produced is capable of recognizing molecules of similar size and molecular weight. This templating could be considered a corona phase analog of the molecular imprinting technique, except that the analyte template is never removed, but remains bound to the backbone, and no-cross-linking is required. See, for example, Ramström, O., Ye, L. & Mosbach, K. Artificial antibodies to corticosteroids prepared by molecular imprinting. *Chem. Biol.* 3, 471-477 (1996), Cheong, S. H. et al. Testosterone Receptor Binding Mimic Constructed Using Molecular Imprinting. *Macromolecules* 30, 1317-1322 (1997), Farber, S., Green, B. S. & Domb, A. J. Selective 17-β-estradiol molecular imprinting. *J. Polym. Sci. Part A Polym. Chem.* 47, 5534-5542 (2009), Hishiya, T., Shibata, M., Kakazu, M., Asanuma, H. & Komiyama, M. Molecularly Imprinted Cyclodextrins as Selective Receptors for Steroids. *Macromolecules* 32, 2265-2269 (1999), Kellens, E. et al. Improved Molecular Imprinting Based on Colloidal Particles Made from Miniemulsion: A Case Study on Testosterone and Its Structural Analogues. *Macromolecules* 49, 2559-2567 (2016), Özgür, E. et al. A new molecular imprinting-based mass-sensitive sensor for real-time detection of 17β-estradiol from aqueous solution. *Environ. Prog. Sustain. Energy* 32, 1164-1169 (2012), and Manickam, P., Pasha, S. K., Snipes, S. A. & Bhansali, S. A Reusable Electrochemical Biosensor for Monitoring of Small Molecules (Cortisol) Using Molecularly Imprinted Polymers. *J. Electrochem. Soc.* 164, B54-B59 (2017), each of which is incorporated by reference in its entirety. A clear advantage is that this gives the newly created binding site direct access to the underlying transducer, which can remain nanometer in scale. The bound appendage should be reversibly displaced upon addition of a more strongly adsorbing analyte. We in fact observe that this is the case for two important steroid sensors: a cortisol sensor, P1-(6,5), and the progesterone sensor, P10-(7,6), as discussed in-depth below.

Figure 1B:
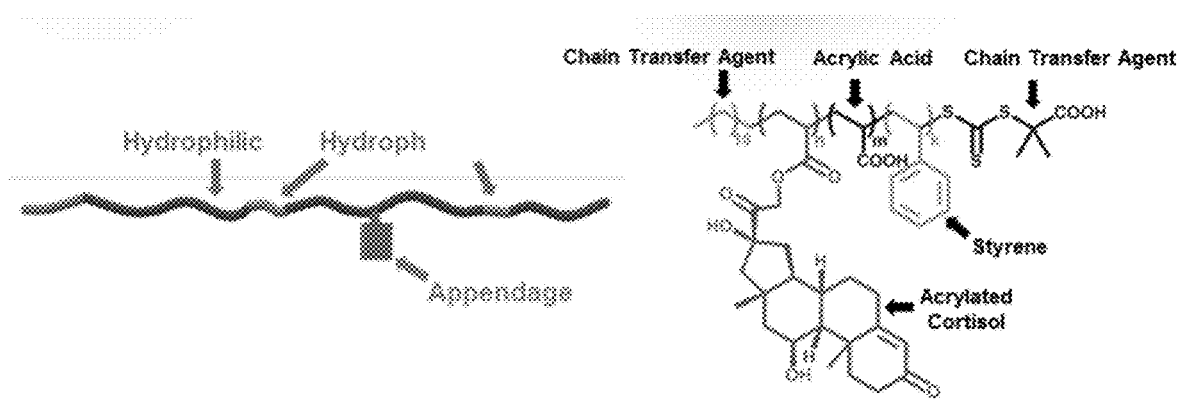
Figure 1C:
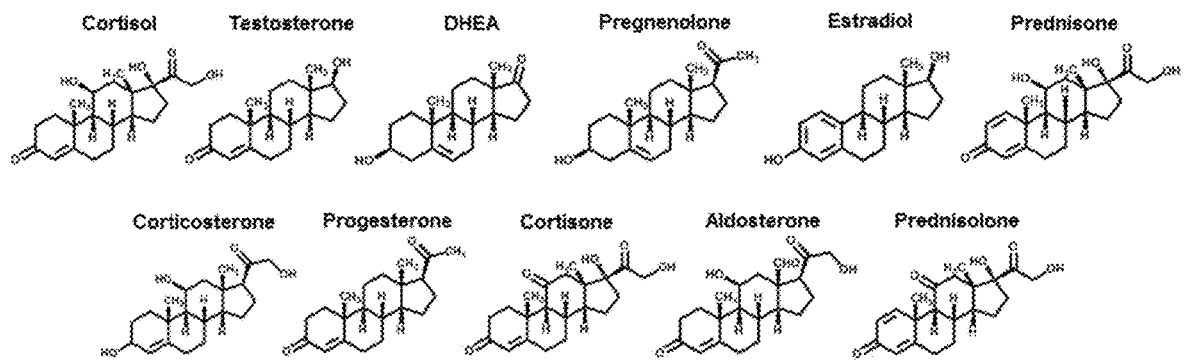

The corona phase library was generated using RAFT polymerization to generate low polydispersity, random copolymers consisting of acrylic acid, styrene, and acrylated cortisol, the chemical appendage. The acrylic acid portion of the backbone provides the hydrophilic units and colloidal stability at physiological pH. The hydrophobic styrene units serve as anchor points for the polymer backbone onto the SWNT (FIG. 1B). The unit composition of the polymers was varied to produce structurally diverse corona phases to sample a range of free-volumes and relative strengths of dynamic binding/unbinding of the appendage. In total, we explore 80 unique corona phases in this work based on 16 polymer backbones to suspend five sets of SWNT chiralities grouped by emission maximum wavelengths: (8,3) and (6,5); (7,5); (10,2); (9,4) and (7,6); and (12,1). These SWNT span a range from 0.75 to 1.0 nm in diameter. These were tested against a panel of 11 steroids, chosen for their physiological and therapeutic significance (FIG. 1C) with the resulting screening results in FIGS. 2A-2F.

Figure 2A:
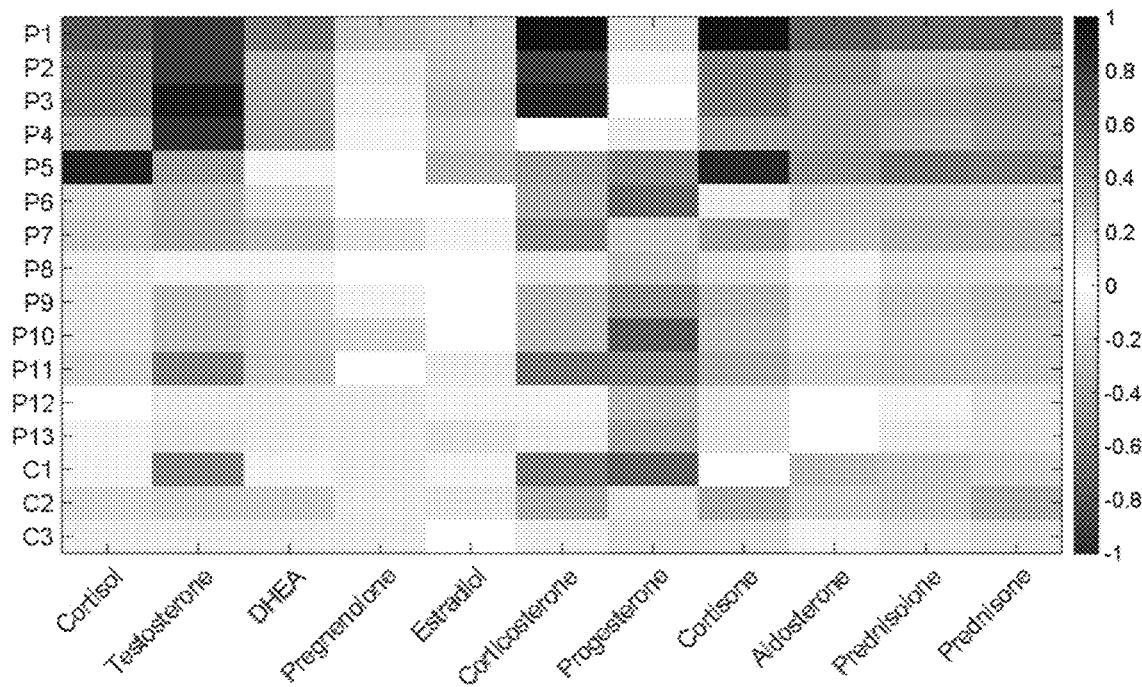
FIGS. 2A-2F show summaries of polymer library screening results.
Figure 2B:
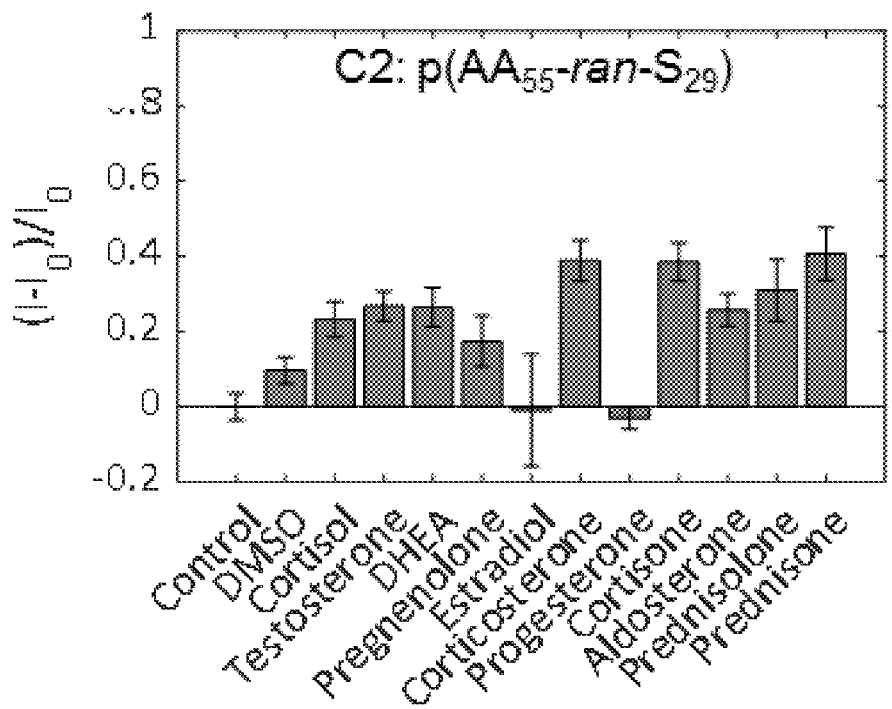
Figure 2C:
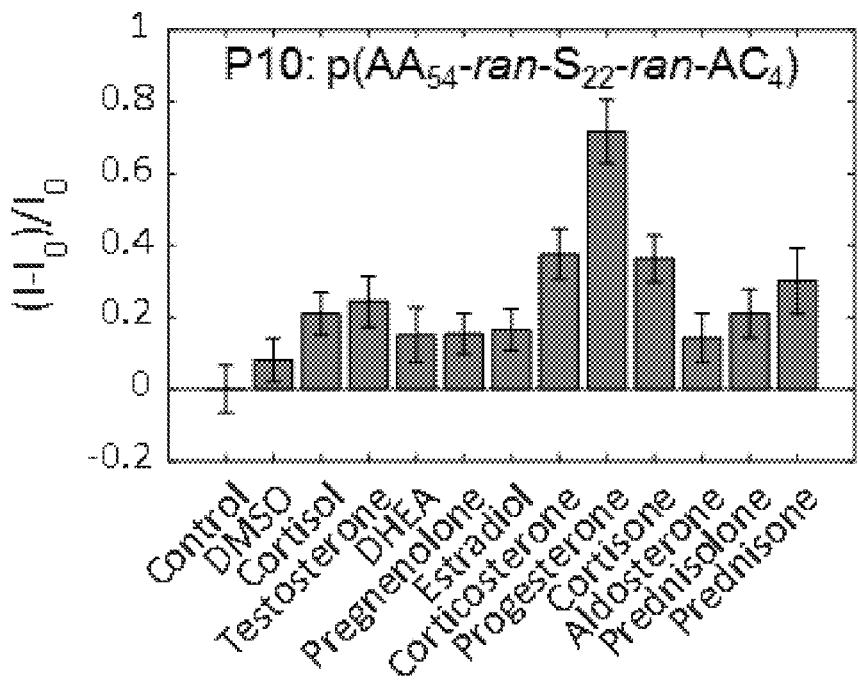

The near-IR fluorescence response of each SWNT wrapped in a distinct polymer corona phase was measured using a solution of 1 mg/L SWNT/corona exposed to 100 µM steroid in 1× PBS containing 2% DMSO for analyte solubility (FIG. 2A). The resulting heat map of binding shows several important trends with varying polymer composition. A comparison between self-templated and non-templated polymers demonstrates increased affinity toward progesterone with greater appendage content in the polymers (FIGS. 2B-2C), supporting this templating approach. As expected, a one-to-one correspondence between appendage structure and analyte selectivity is not observed. The appendage was based around the molecular structure of cortisol—which shares the three concatenated, 6-membered rings with one pentamer ring with the entire steroidal set considered in this work. The resulting selectivity for progesterone suggests that it has a stronger affinity for the resulting cavity upon appendage desorption. The screening results in FIGS. 2A-2F point to two corona phases of particular interest in this current study.

Figure 2D:
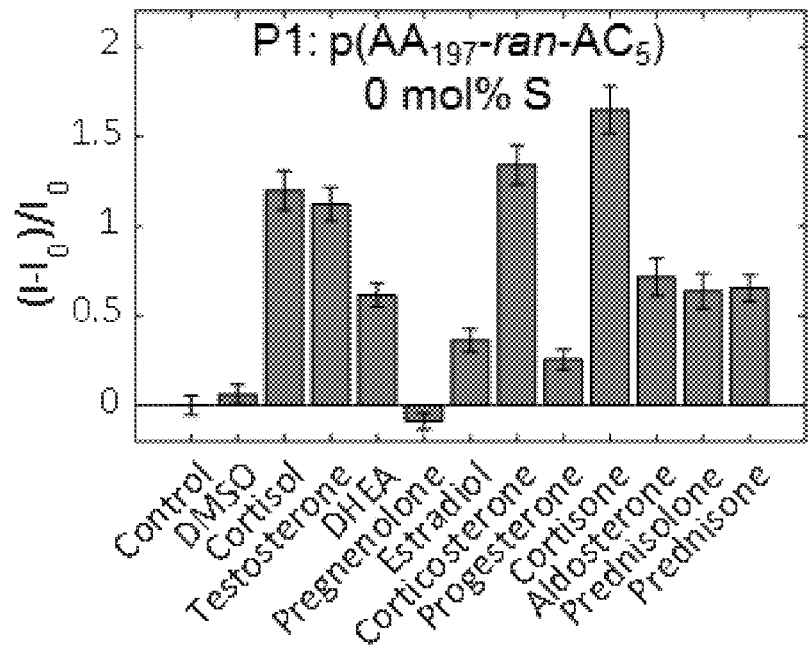
Figure 2E:
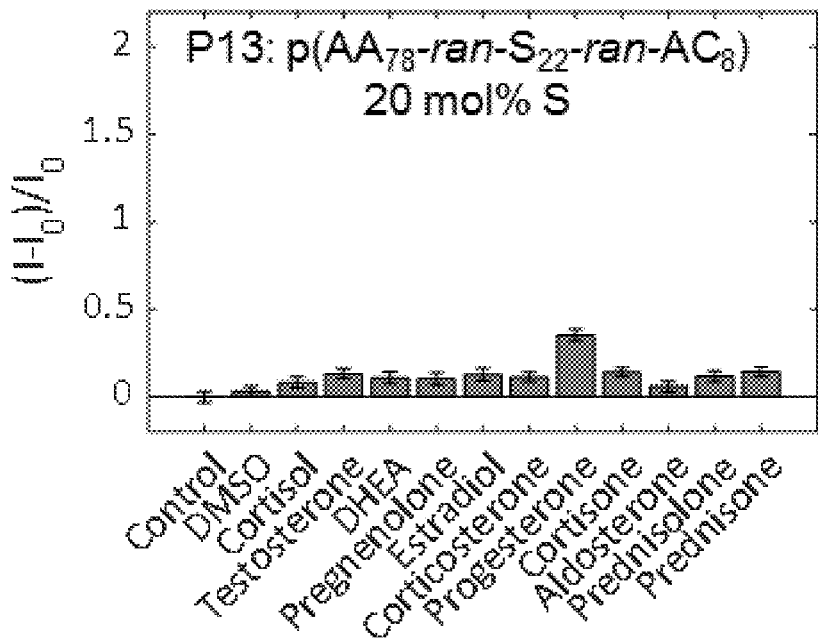
Figure 2F:
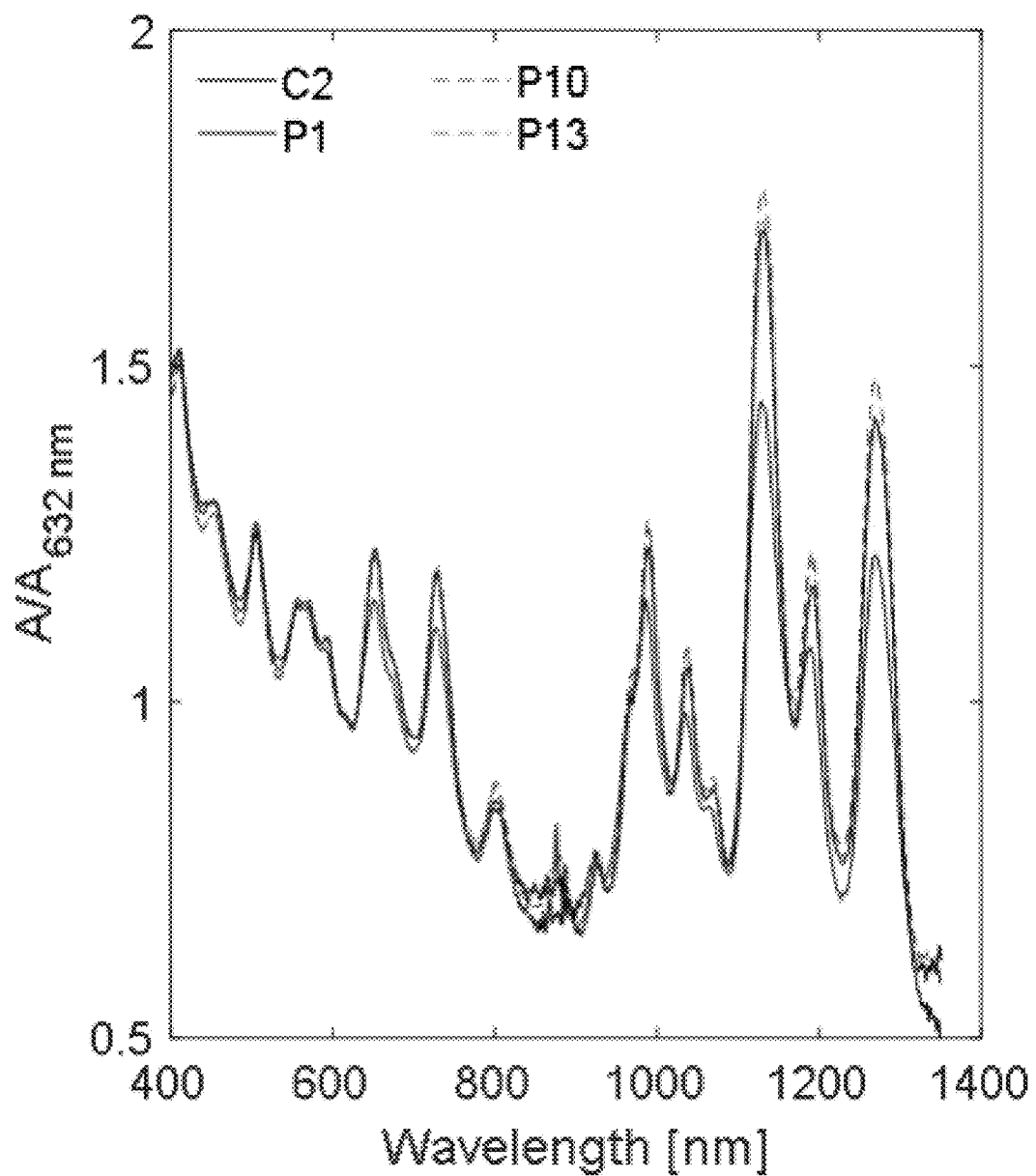

Increasing styrene content systemically decreases nIR fluorescence response to analyte binding for the entire steroid library (FIGS. 2D-2E). As an anchor for the polymer corona, styrene is shown to influence the responsivity in two ways. Styrene itself can sterically block interactions between the analyte and the SWNT surface by occupying surface area otherwise accessible for adsorption. Second, styrene serves as an anchor for the polymer backbone by design, and its increasing density necessarily constrains the mobility of the corona phase. We expect that with increasing styrene frequency along the backbone aggregation of the analyte. We ruled out aggregation and colloidal instability as an alternative hypothesis for the observed selectivity. The UV-Vis-NIR photoabsorption spectra of the SWNT/corona systems that comprise the heat map of responses show well-resolved $E_{11}$ and $E_{22}$ photoabsorption transitions, consistent with colloidal dispersion in contrast to aggregation (FIG. 2F). See, for example, Choi, J. H. & Strano, M. S. Solvatochromism in single-walled carbon nanotubes. *Appl. Phys. Lett.* 90, 223114 (2007), which is incorporated by reference in its entirety. SWNT aggregation also causes nIR fluorescence quenching. See, for example, Weisman, R. B. in *Carbon Nanotubes: Quantum Cylinders of Graphene* (eds. Saito, S. & Zettl, A. B. T.-C. C. of C. M. S.) 3, 109-133 (Elsevier, 2008), which is incorporated by reference in its entirety.

Figure 3A:
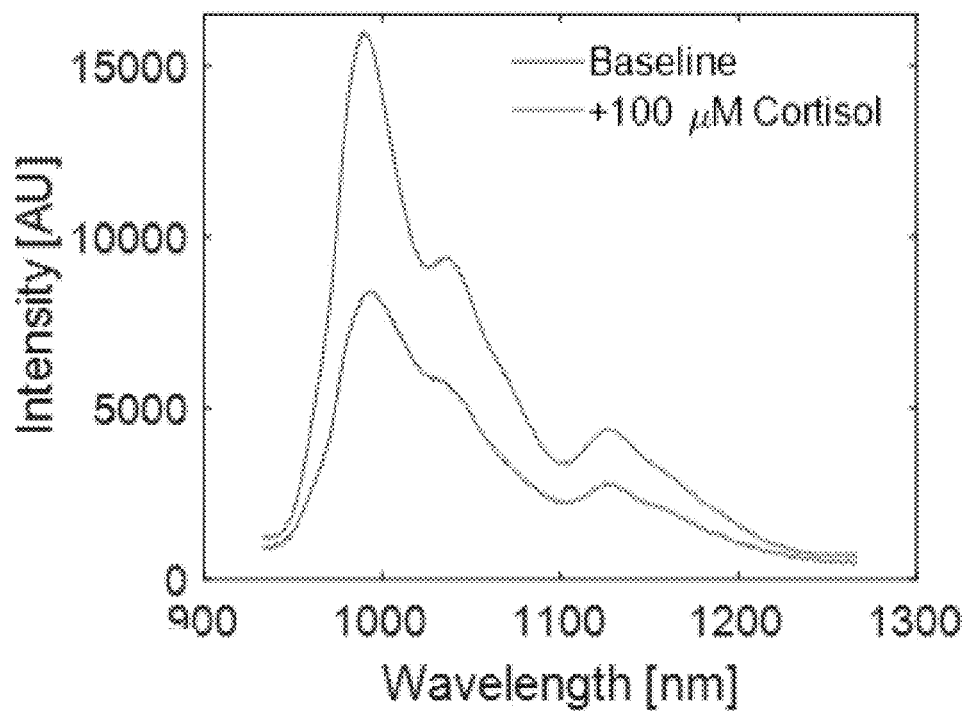
FIGS. 3A-3H shows sensor performance in solution phase.
Figure 3B:
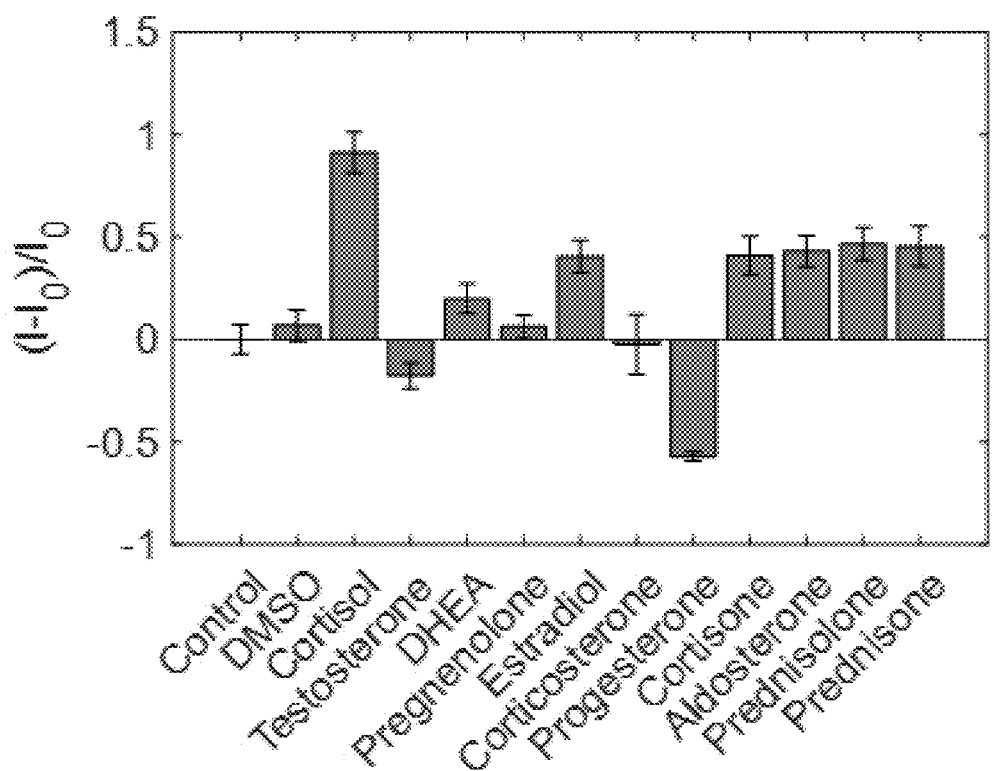
Figure 3C:
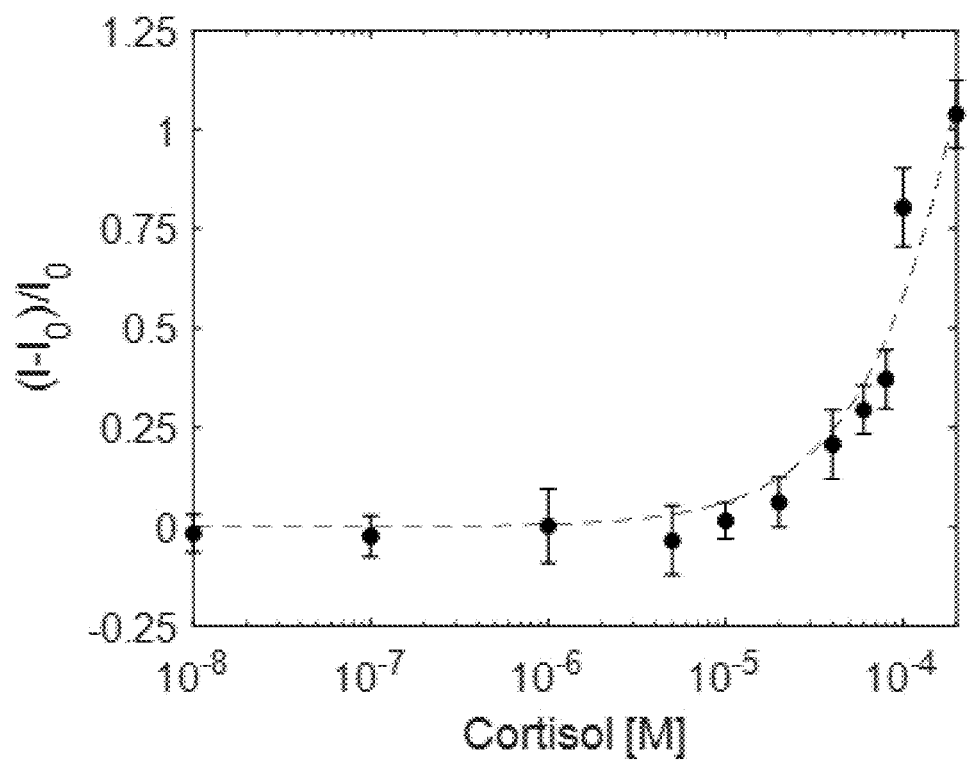

Two SWNT corona phases with high selectivity were examined: P1-(6,5) for cortisol and P10-(7,6) for progesterone. The first, P1-(6,5) consists of a (6,5) chirality SWNT wrapped by p($AA_{197}$-ran-$AC_5$) polymers and exhibit a 90% turn-on fluorescence response to cortisol (FIG. 3A), whereas the magnitude of the second highest response was 57% at 100 µM (FIG. 3B). The sensor was exposed to varying cortisol concentrations, and the response was fit to the following functional form:

$$\frac{I - I_0}{I_0} = \beta \frac{C}{C + K_D} \quad (1)$$

Where I is the fluorescence intensity after steroid addition, $I_0$ is the original intensity, $\beta$ is the gain, C is the steroid concentration, and KD is the equilibrium dissociation constant (FIG. 3C). A solution of 1 mg/L SWNT found responsivity between 10-200 µM. The calibration curve was not extended beyond 200 µM due to solubility, which precluded a meaningful KD value from being calculated.

Figure 3D:
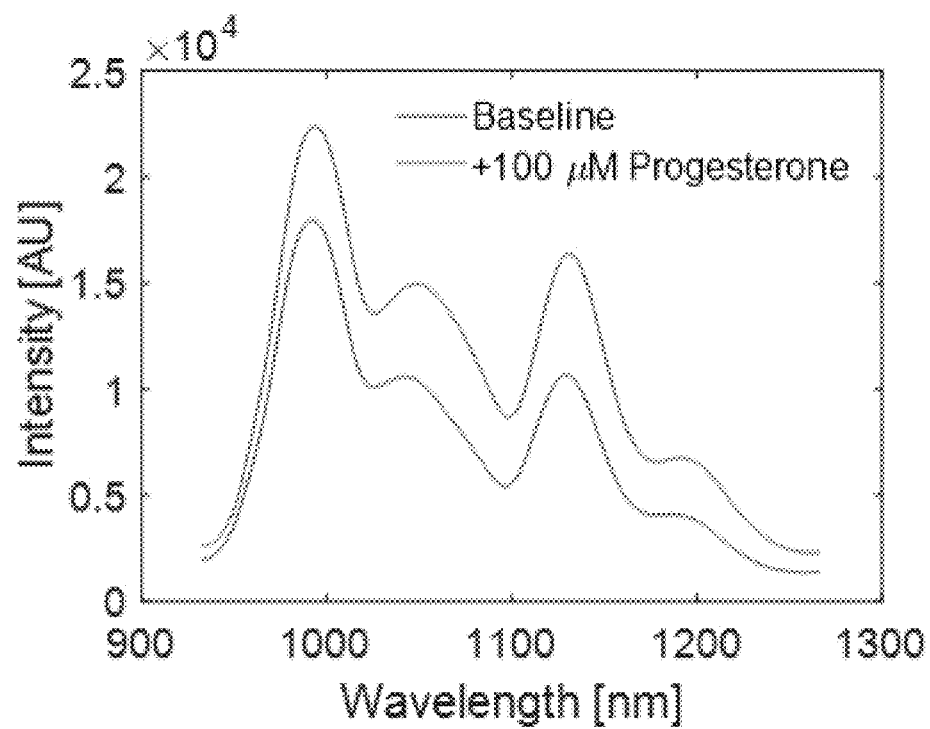
Figure 3E:
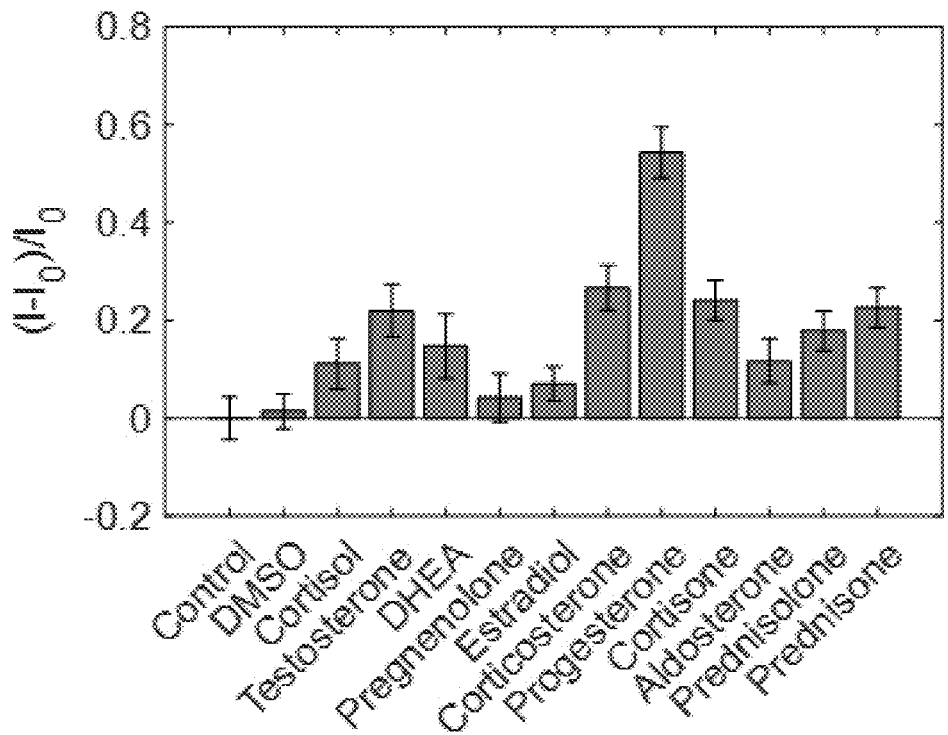
Figure 3F:
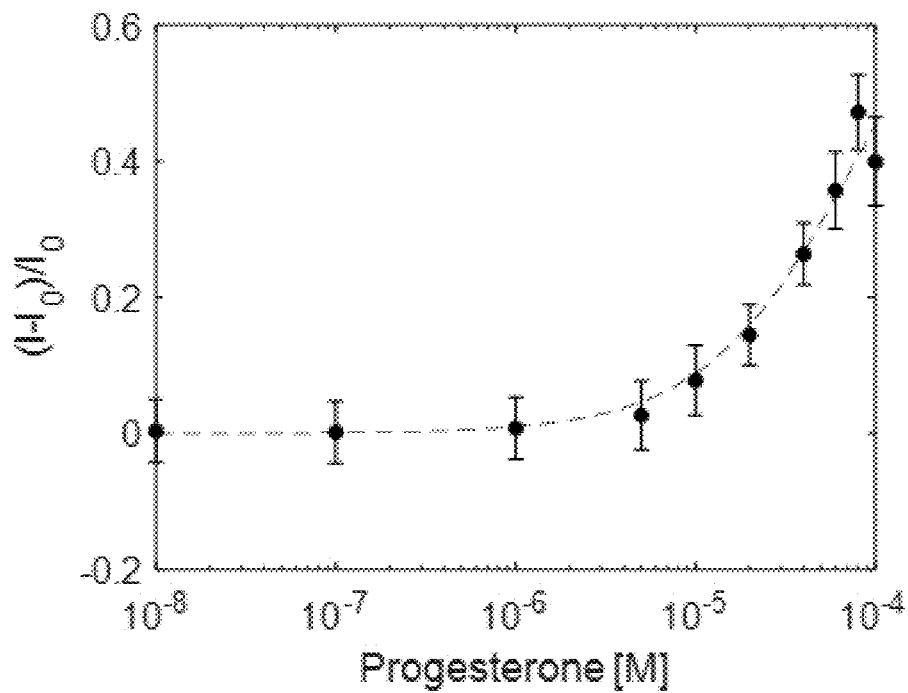
Figure 3G:
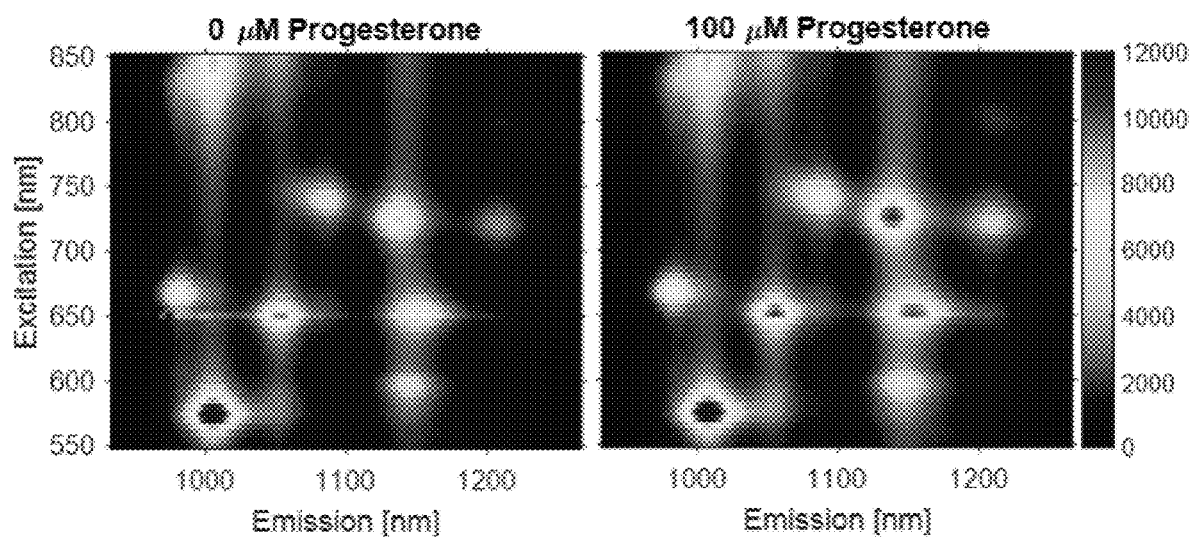

The second corona phase, P10-(7,6), is selective to progesterone and comprised of a SWNT wrapped with p($AA_{53}$-ran-$S_{22}$-ran-$AC_4$) polymer (FIG. 3D). The response appears strongly chirality dependent, with the (9,4) and (7,6) fluorescence peaks having the strongest response at 72%, while the remaining chiralities also exhibited a less intense turn-on response. The sensor exhibited some selectivity with the next highest responses inducing only a 38% fluorescence increase at 100 µM (FIG. 3E). The calibration curve shows sensor responses between 5-100 µM and a $K_D$ of 100 µM (FIG. 3F). An nIR fluorescence excitation-emission map taken before and after the addition of 100 µM confirms that the (9,4) and (7,6) chiralities are the most sensitive to progesterone (FIG. 3G).

Figure 3H:
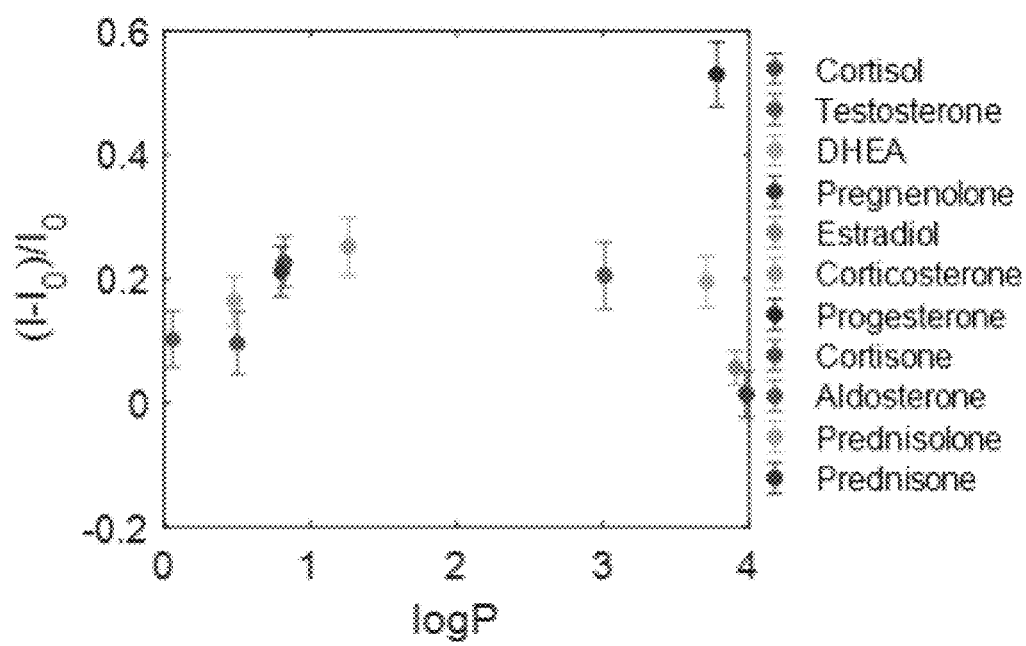

Despite the common structural features with the other steroids, progesterone and cortisol produced higher sensor responses by factors of 1.9 and 1.6 and at 100 uM, respectively. No trends were observed when considering the oxidation state of each steroid, as well as the spatial distribution of oxygen groups on the backbone. Furthermore, we rule out the possibility of a non-specific hydrophobic interaction, as progesterone appears as an outlier when considering its response vs. its logP value (FIG. 3H).

These results show that the corona phase itself discriminates between steroids based on their specific molecular shape and chemical display. The curvature of the SWNT surface appears to influence the resulting corona phase binding. Diameter dependence can show that curvature influences the pocket size and selectivity. The acrylic acid composition is capable of hydrogen bonding with hydroxyls and carbonyl groups on steroids, with smaller amounts of anchoring styrene monomers decreasing the spatial proximity of these H-bonding groups to each other and distance from the SWNT surface. Furthermore, the tethered appendages interact with the SWNT via hydrophobic interactions and with acrylic acids via H-bonding. The same polymer will adopt a different conformation on each SWNT chirality due to local curvature. Taken together, each corona is distinct and will interact with each steroid to a different degree. While the steroids share the same overall 4-alkyl ring backbone, they are distinct in the distribution of hydroxyl groups, carbonyls, and alkyl chains. Due to their hydrophobicity, the alkyl rings, alkyl chains, and methyl groups likely sit flat on the SWNT surface, while atoms in proximity to more polar groups like hydroxyls and carbonyls extend out into solution. Therefore, each steroid has a unique shape on the SWNT surface, which dictates the extent it can fit into a given corona phase.

Figure 4A:
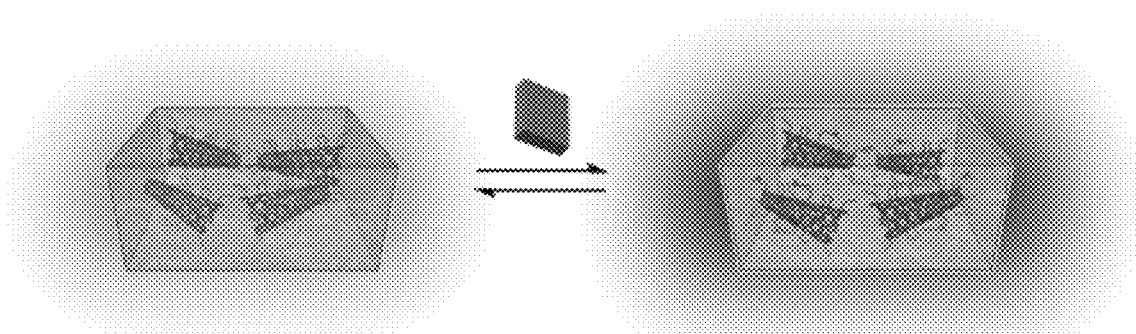
FIGS. 4A-4G depict hydrogel formulation, selection, and performance.
Figure 4B:
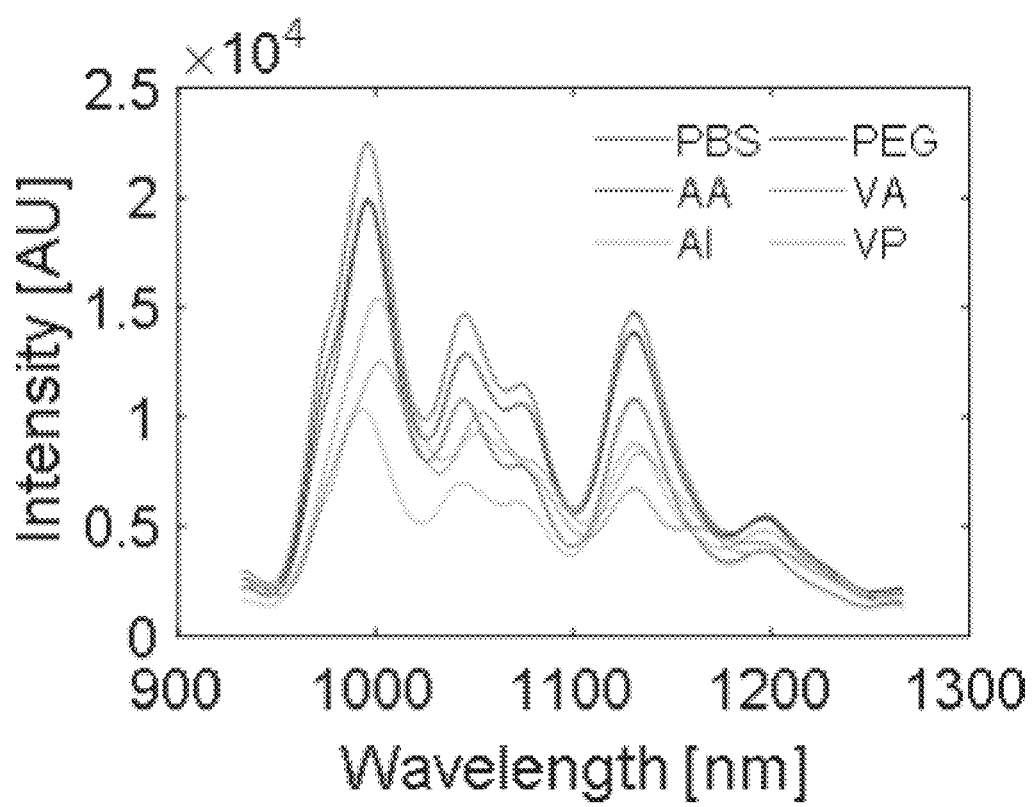
Figure 4C:
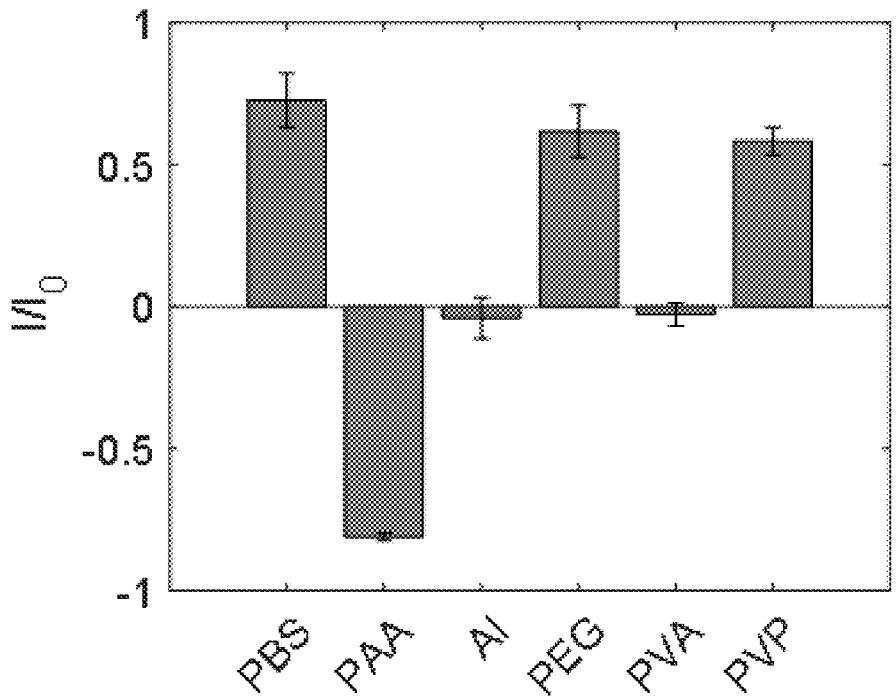

Hydrogel Characterization. To provide a biocompatible interface and a localizable implant that can be queried at any time in vivo, the progesterone sensor was tested in a variety of hydrogel materials (FIG. 4A). Hydrogels have been made using a variety of materials, including polyacrylamide, PEG, poly(acrylic acid), poly(vinyl pyrrolidone), and alginate. See, for example, Iverson, N. M. et al. Quantitative tissue spectroscopy of near infrared fluorescent nanosensor implants. *J. Biomed. Nanotechnol.* 12, 1035-1047 (2016), which is incorporated by reference in its entirety. To choose the hydrogel, solution phase SWNT were mixed with the uncrosslinked polymers, and the responses to 100 µM progesterone were measured. Without progesterone, PEG had the least effect on baseline fluorescence, indicating the best preservation of the CoPhMoRe phase (FIG. 4B). The other polymers inducing larger intensity and/or wavelength shifts. Furthermore, only the samples with PEG and PVP had identical responses to 100 µM progesterone as the sensor in 1× PBS (FIG. 4C). For these reasons, PEG was chosen as the encapsulating material for the progesterone sensor.

Figure 4D:
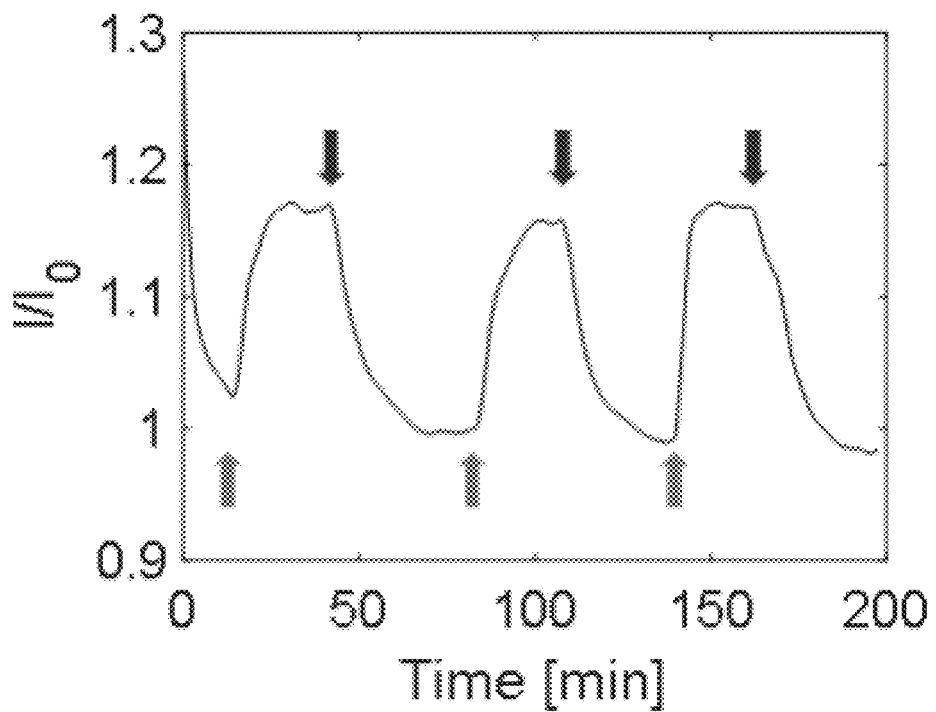
Figure 4E:
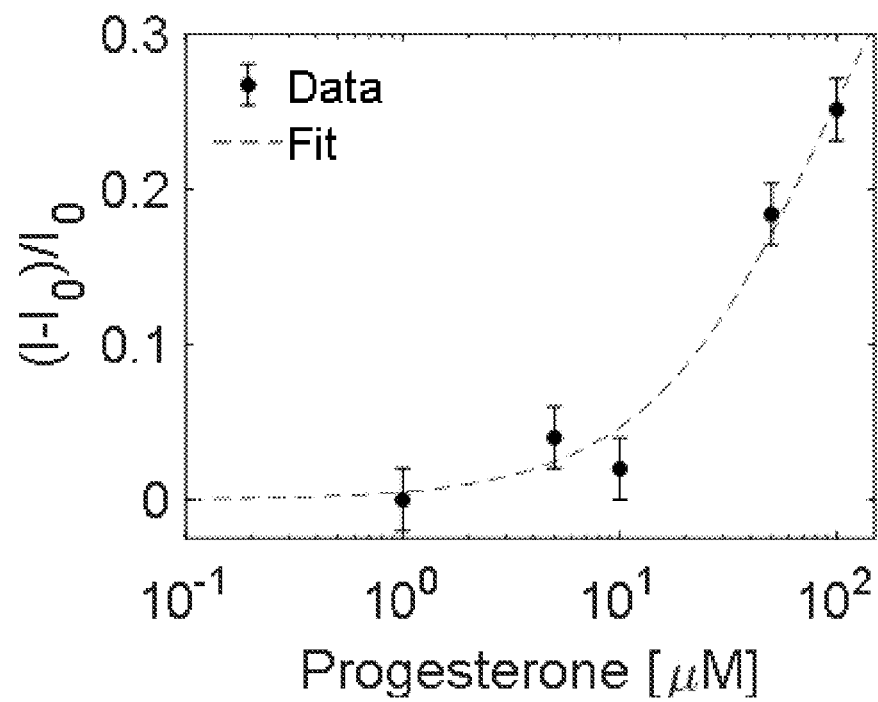
Figure 4F:
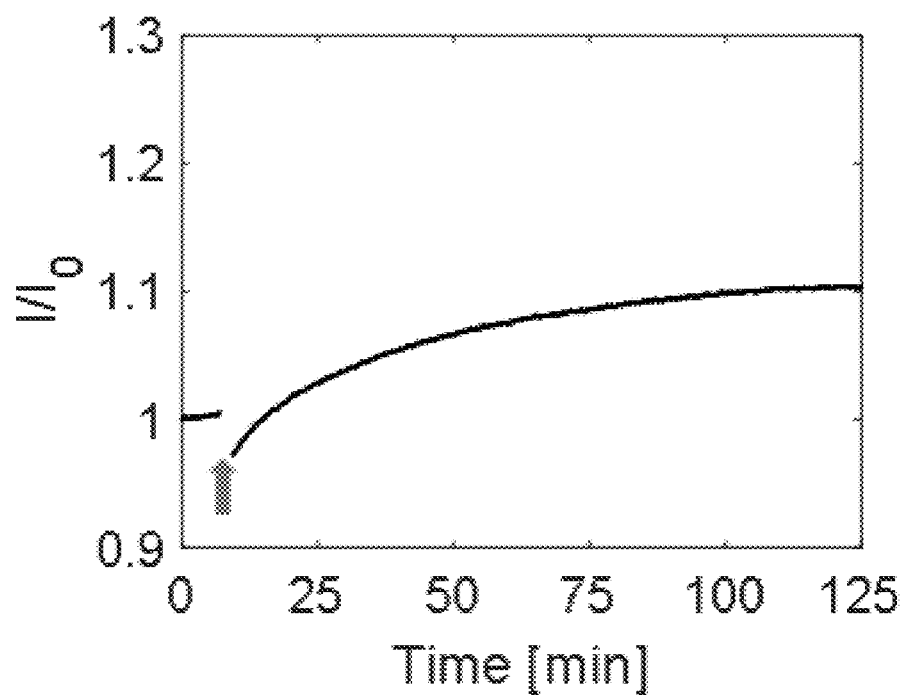
Figure 4G:
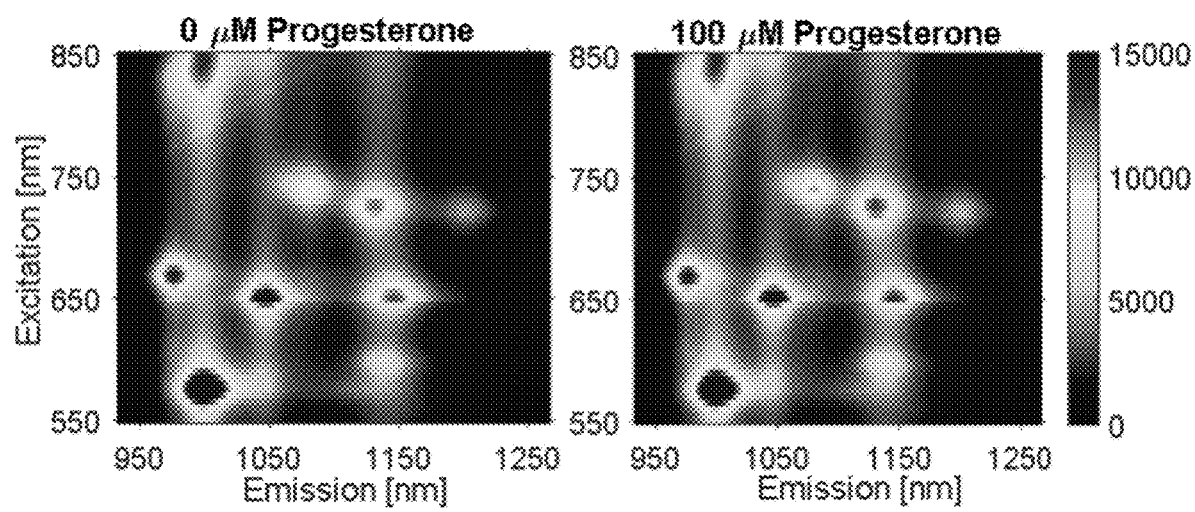

The functionality of the sensor in the hydrogel was verified through several tests. The hydrogel was exposed to alternating cycles of 0 and 100 µM progesterone in 1× PBS (FIG. 4D). The hydrogel exhibited a stable and reversible response with a constant baseline. The stable baseline allows perturbations in fluorescence to be attributed to changes in analyte concentration rather than sensor artefacts. The sensor hydrogel's fluorescence response was also calibrated against progesterone (FIG. 4E). After being equilibrated in 10% mouse serum in 1× PBS, the sensor still responded to 100 µM progesterone (FIG. 4F). The magnitude of the response was lower at 12%, but reversibility was maintained. The lower response in the biological environment suggests the presence of interfering molecules that reduce sensor sensitivity. Nevertheless, these interfering molecules may be avoided with strategic placement of the sensor. For example, implanting the hydrogel in the interstitial space as opposed to intravascularly avoids proteins such as albumin, which non-specifically binds to a number of surfaces. See, for example, Adamczyk, Z., Nattich-Rak, M., Dąbkowska, M. & Kujda-Kruk, M. Albumin adsorption at solid substrates: A quest for a unified approach. *J. Colloid Interface Sci.* 514, 769-790 (2018), which is incorporated by reference in its entirety. As indicated by the excitation-emission map, the most sensitive chiralities in the hydrogel were still the (10,2), (9,4), and (7,6), as in solution phase (FIG. 4G).

The hydrogel-encapsulated SWNT exhibit a lower magnitude of response to progesterone at 30% versus the 60% observed in solution phase. Several contributions may exist. First, as the hypothesized mechanism involves displacement of the suspending polymer on the SWNT surface, the crosslinked hydrogel matrix may reduced sensor sensitivity by constraining the movements of the suspending polymer. Second, the free radicals produced during hydrogel fabrication may have chemically altered the suspending polymer on the SWNT, which were produced using RAFT polymerization and are living.

In vivo proof of concept. As a proof of concept of in vivo measurements of progesterone with the CoPhMoRe sensor, hydrogels with and without a dialysis bag were implanted subcutaneously into mice. Analytes would be able to pass freely into and out of the hydrogel through contact with the interstitial fluid.

Figure 5A:
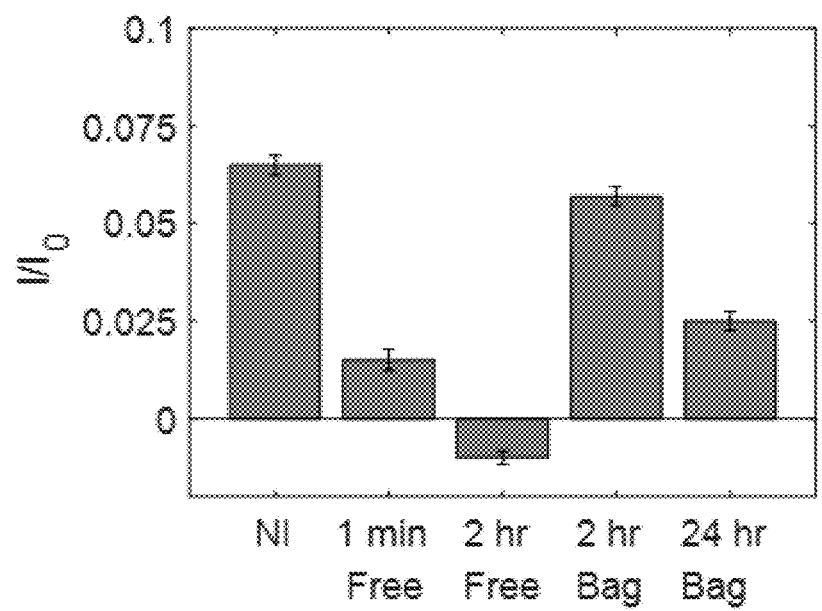
FIGS. 5A-5G depict a proof of concept of in vivo steroid sensor monitoring.
Figure 5B:
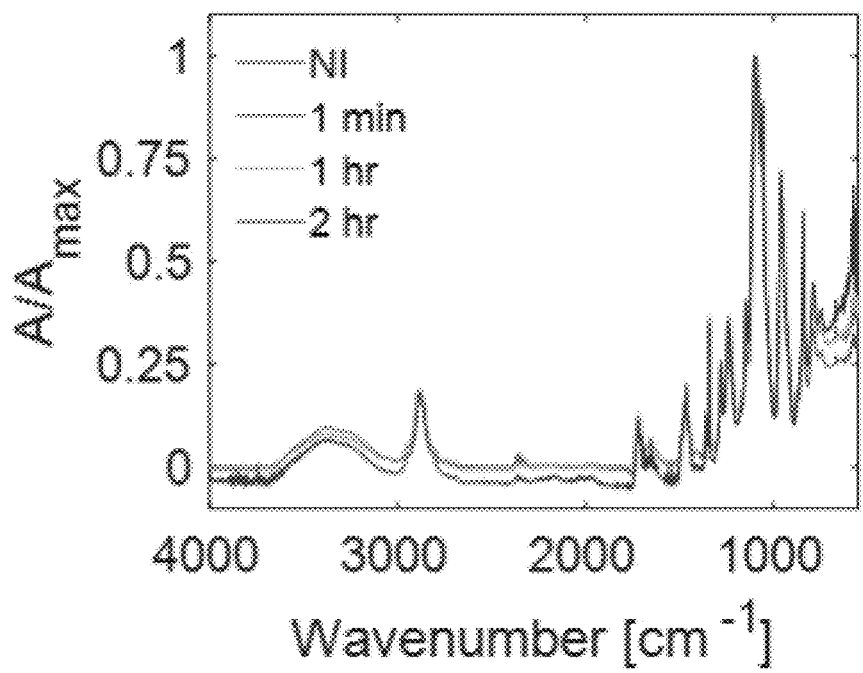

Sensor hydrogels implanted without dialysis bags were deactivated upon implantation in a time dependent manner (FIG. 5A). Compared to hydrogels subjected to the same sterilization procedure but not implanted, hydrogels that were implanted into a mouse, extracted, and tested in vitro were completely insensitive to 100 µM progesterone after two hours. Conversely, when extracted within 2 hours and tested outside the mouse, hydrogels inside of 6-8 kDa dialysis bags still responded to 100 µM progesterone with the same magnitude as the control. After 24 hours in the mouse, the hydrogel was only partially deactivated. The deactivation of the hydrogel suggests the presence of an interfering molecule in vivo that either chemically alters or binds irreversibly to the CoPhMoRe site. Given that the sensor functions in mouse serum, the interferents are likely inflammatory molecules released at the implantation site during surgery. Furthermore, the kinetics of deactivation with dialysis bag over 24 hours suggest that at least one of the interferents has a molar mass on the order of 5 kDa. A number of different molecules are released in the acute inflammatory response, including cytokines, protein fragments, reactive oxygen and nitrogen species, etc. See, for example, Dang, T. T., Nikkhah, M., Memic, A. & Khademhosseini, A. in *Natural and Synthetic Biomedical Polymers* (eds. Kumbar, S. G., Laurencin, C. T. & Deng, M. B. T.-N. and S. B. P.) 309-331 (Elsevier, 2014). doi:https://doi.org/10.1016/B978-0-12-396983-5.00020-X, which is incorporated by reference in its entirety. To rule out biofouling of the bulk hydrogel as the deactivation mechanism, the zwitterionic component 2-methacryloyloxyethyl phosphorylcholine (MPC) was added to the hydrogel formulation, verified to work in vitro, and again found to be deactivated after implantation into mice. The strong non-fouling attributes of MPC in PEG hydrogels have been reported in previous studies, and the deactivation suggests that biofouling is not the predominant mechanism. See, for example, Herrick, W. G. et al. PEG-Phosphorylcholine Hydrogels As Tunable and Versatile Platforms for Mechanobiology. *Biomacromolecules* 14, 2294-2304 (2013), which is incorporated by reference in its entirety. To determine the presence of any chemical modification, FTIR measurements were performed on the hydrogels (FIG. 5B). Due to the low mass concentration, the SWNT and the suspending polymers are not visible in the IR spectra. However, the bulk hydrogel spectra before and after sensor deactivation are identical. Therefore, chemical modification of the bulk hydrogel is not the primary mechanism of deactivation.

Figure 5C:
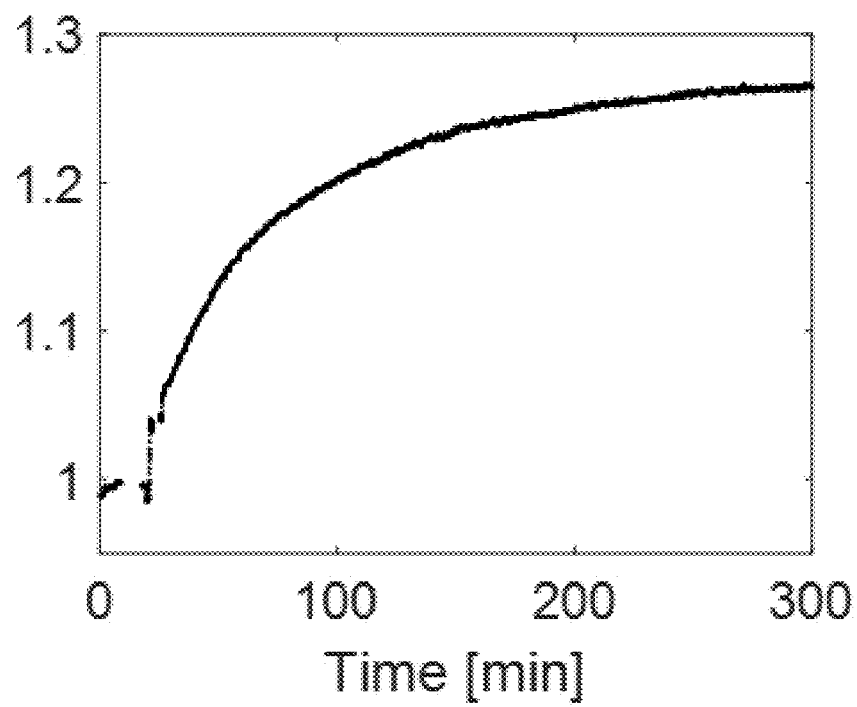

Nevertheless, the delay of deactivation by using a 6-8 kDa dialysis bag permitted a 24-hour window in which our sensor could be tested in vivo. The response profile to 100 µM progesterone in vitro was measured (FIG. 5C). The equilibrium response was 27% and leveled out after 3 hours.

Figure 5D:
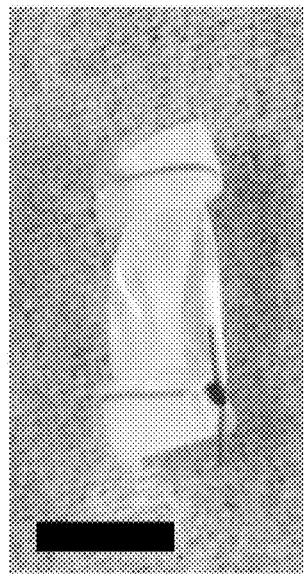
Figure 5E:
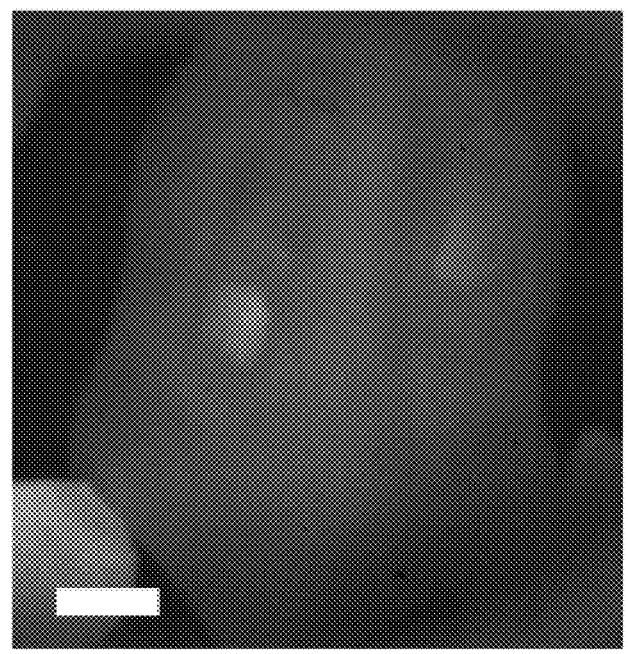
Figure 5F:
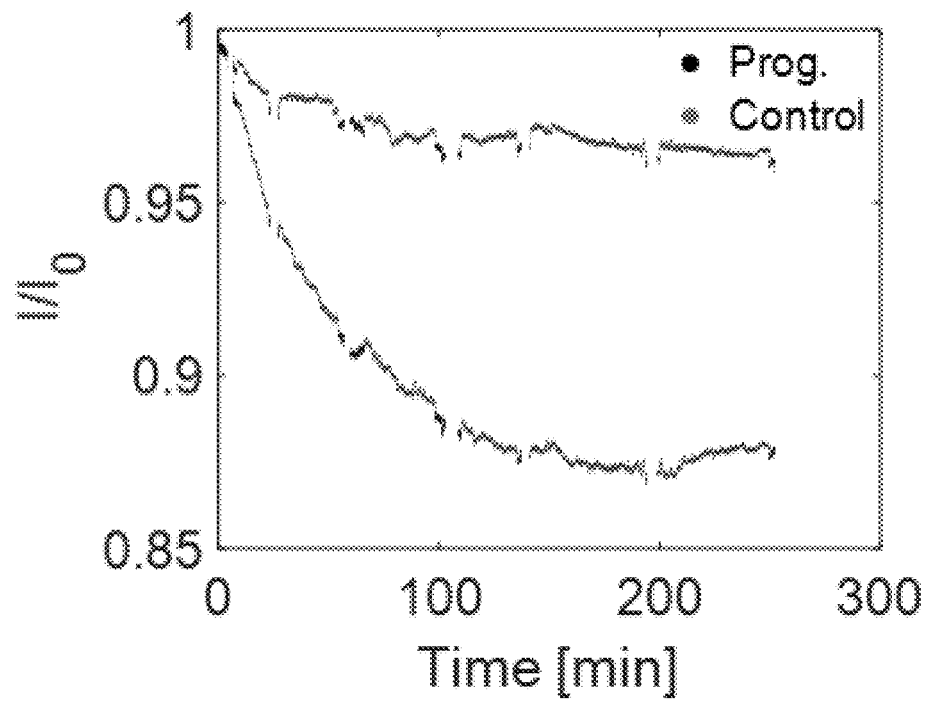
Figure 5G:
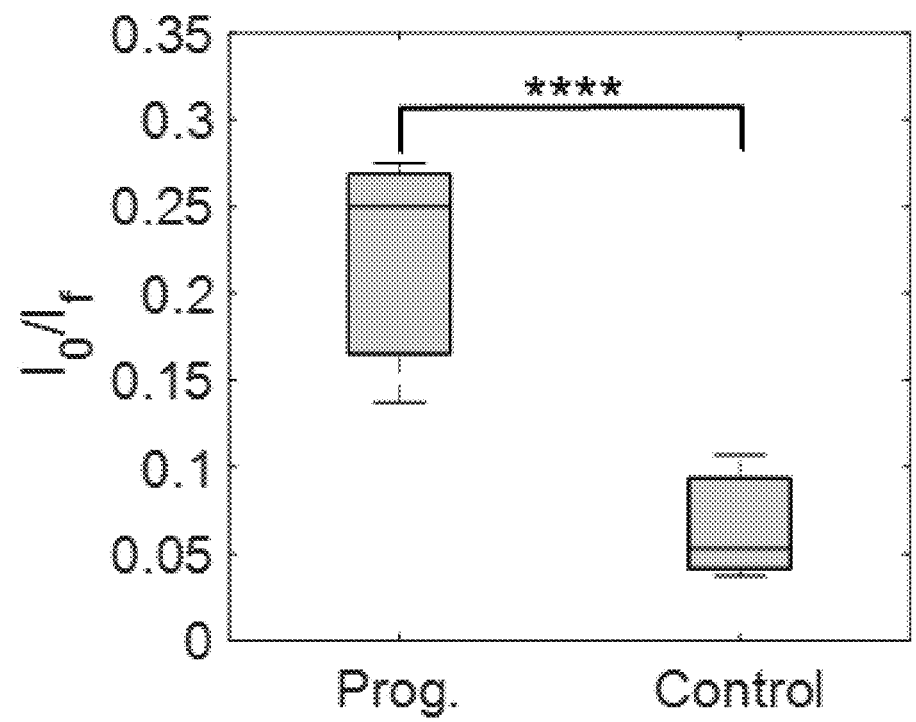
Figure 6A:
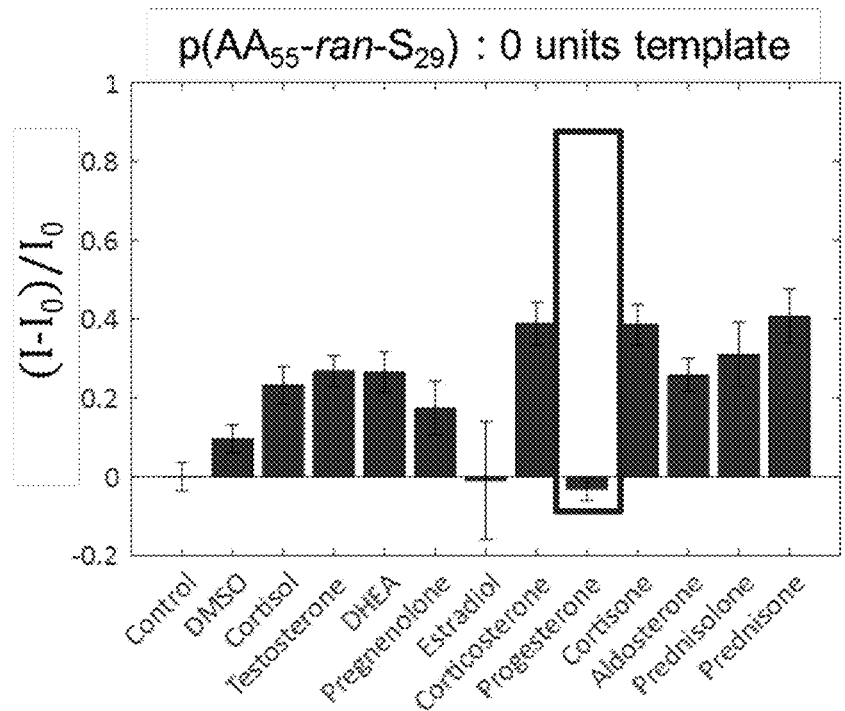
FIGS. 6A-6C show increasing template percentage increases sensitivity to some steroids.
Figure 6B:
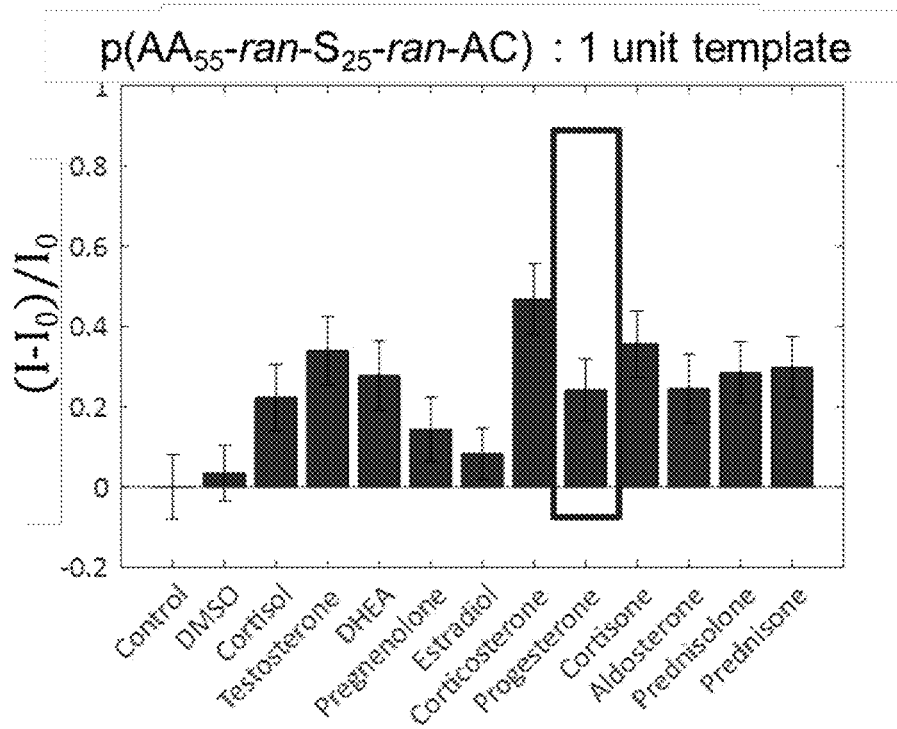
Figure 6C:
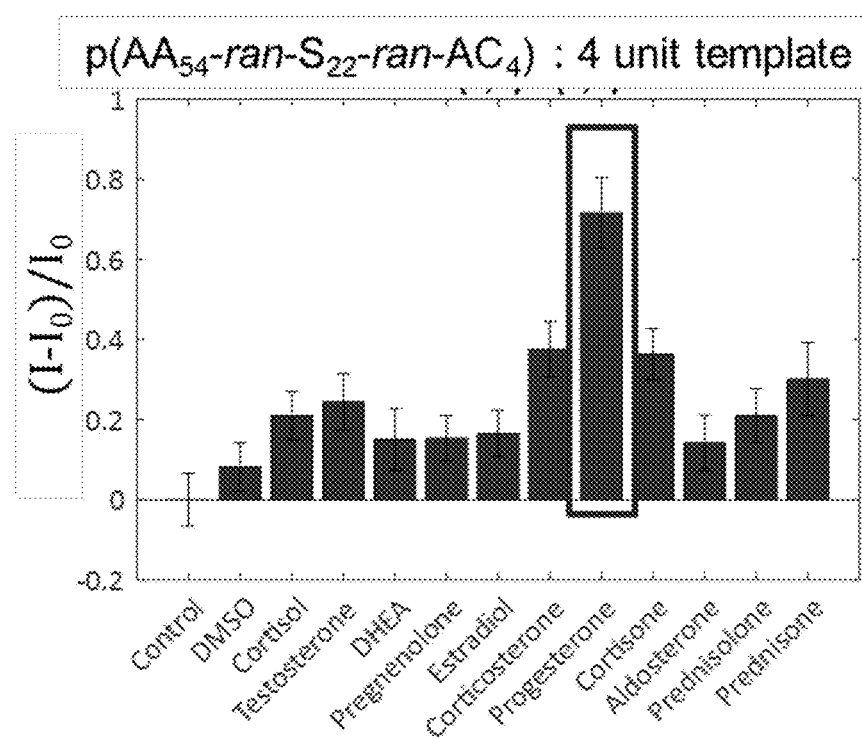

Two dialysis bags—one incubated in 100 µM progesterone and another incubated in 0 µM progesterone for three hours—were implanted simultaneously in multiple mice to test the short-term functionality of the sensors in vivo (FIGS. 5D-5E). The in vivo trial exploited the reversibility of the sensor by measuring a decrease in fluorescence as progesterone diffuses out from the hydrogel (FIGS. 5A-5G). The sensor incubated in buffer served as a control to measure any perturbations in sensor due to the change in environment from buffer to interstitial fluid. In each trial, the sensor incubated in progesterone showed a higher decrease in fluorescence relative to its paired control (FIG. 5F). Over three mice, the sensor response was 22.1±6.6%, and the control was 7.4±3.7%. The difference was statistically significant with a one-tailed p-value of 0.016 (FIG. 5G).

The reversal monitoring demonstrates functionality of the sensor while working in the time constraint of deactivation. In its current form, the sensor will only function in the first day when implanted in vivo. The eventual application is long-term monitoring of steroids, so the interferent will be identified in future work. Therefore, the sensor formulation will be modified to mitigate the deactivation, as well as to decrease the limit of detection to target physiological values of progesterone. Physiological concentrations of cortisol and progesterone in typical people are lower than the dynamic range of the sensor. Cortisol exists between 0-500 nM,[4] while progesterone can range from 0 to 800 nM depending on the status of pregnancy. See, for example, Lee, M. A., Bakh, N., Bisker, G., Brown, E. N. & Strano, M. S. A Pharmacokinetic Model of a Tissue Implantable Cortisol Sensor. *Adv. Healthc. Mater.* 5, 3004-3015 (2016), Dunning, M. B. & Fischbach, F. *Nurses' Quick Reference to Common Laboratory & Diagnostic Tests.* (2010) and Booth, M. & El Garf, T. A. R. Plasma Progesterone Concentration During the Third Trimester of Diabetic Pregnancy. *BJOG An Int. J. Obstet. Gynaecol.* 81, 768-776 (1974), each of which is incorporated by reference in its entirety.

In total, these experiments demonstrate both the feasibility and efficacy of the development process that originates with CoPhMoRe library synthesis and discovery, characterization, insertion into a biocompatible interface, and in vivo measurement. Hence, this work underscores a new strategy for in vivo bioanalyte monitoring and motivates further development to broaden the classes of measured biomarkers and their measurable concentrations. In the steroid space, future research avenues exist. To permit long-term monitoring of progesterone, the sensor deactivation mechanism will be elucidated, and interfering molecules will be identified. Additionally, the limit of detection of the progesterone sensor will be decreased to enable monitoring of the entire dynamic range of the analyte. Furthermore, the tunability of the template steroid system and hydrogel formulations will be further explored to construct sensors for other steroid hormones. In this way, several unique sensors for a range of bioanalytes can be constructed to enable multiplexed biomarker measurements to compose a comprehensive evaluation of an individual's health.

Experimental

Materials. Raw single wall carbon nanotubes (SWNT) produced by the HiPCO process were purchased from NanoIntegris and used without further processing (Batch HR27-104). Poly(ethylene glycol) diacrylate (PEGDA) ($M_n$=8000) was purchased from Alfa Aesar. All other chemicals were purchased from Sigma Millipore.

Acrylation of Cortisol. Cortisol (2 grams, 1 equiv.) and triethylamine (850 mL, 1.1 equiv.) was dissolved in 50 mL tetrahydrofuran (THF). The solution was placed in an ice-bath under magnetic stirring. Acryloyl chloride (0.5 mL, 1.1 equiv.) diluted in THF at 10 vol % was added dropwise to the solution. The reaction proceeded at 0° C. for 1 hour and at room temperature thereafter for two days. The solution was decanted from the HCl-TEA salts. THF was removed by rotary evaporation. The product was reconstituted in 50 mL dichloromethane (DCM), washed thrice with 0.5 M HCl, twice with 5 wt % $NaHCO_3$, and once with saturated aqueous NaCl. The solution was dried using anhydrous $NaSO_4$. DCM was removed by rotary evaporation. 1.2 grams of product was obtained. The structure was confirmed using $^1$H NMR using a Bruker AVANCE III -400 NMR Spectrometer.

Polymer Library Synthesis. Varying amounts of styrene (S), acrylic acid (AA), and acrylated cortisol (AC) monomers were dissolved in 10 mL 1,4-dioxane according to the specific polymer design. MEHQ in acrylic acid and 4-tert-butylcatechol in styrene were removed by passing the reagents through columns packed with inhibitor removers. 2-(Dodecylthiocarbonothioylthio)-2-methylpropionic acid (1 equiv.) and 2,2'-Azobis(2-methylpropionitrile) (0.2 equiv.) were added to each reaction mixture. The solution was sparged with $N_2$ for 30 minutes and sealed in the nitrogen environment throughout the reaction. The reaction was conducted at 70° C. for 24 hours. After the reaction, the mixture was precipitated in 300 mL diethyl ether. The polymer was redissolved in THF and re-precipitated in diethyl ether twice more to remove unreacted monomer. The polymer was dried under vacuum for 3 days and stored at −20° C. until further use.

Polymer Characterization. NMR spectra were obtained by dissolving polymers at 30 mg/mL in methanol-d4. Molecular weight distributions were obtained using gel permeation chromatography on an Agilent Infinity 1260 equipped with a PL Aquagel-OH 30 column. The mobile phase was an aqueous solution of 0.2 M $NaNO_3$ and 0.01 M $NaH_2PO_4$ eluted at a flowrate of 0.5 mL/min. Samples were dissolved at 5 mg/mL, adjusted to pH 7, and filtered through a 0.22 um membrane prior to the run. The molar mass was calibrated against PEG standards ranging from 106 to 30,310 Da. FTIR spectra were measured from 500-4000 $cm^{-1}$ with a Nicolet 4700 (Thermo Scientific).

SWNT Suspension. In 5 mL of 1× PBS, 5 mg HiPCO SWNT and 50 mg of polymers were mixed. The solution was adjusted to a final pH of 7.4 using 2 M NaOH. The mixture was bath sonicated for 10 minutes and ultrasonicated using a 6 mm probe at a power of 10 W for 1 hour (QSonica). The resulting suspension was ultracentrifuged at 155,000 rcf for four hours. The top 80% of the suspension was reserved for further use, while the remaining 20% was discarded. Free polymer was removed from the suspension by dialysis against 1× PBS over 5 days using 100 kDa cutoff Float-a-Lyzer devices (Spectrum Labs) with buffer replacements thrice daily. UV-Vis-NIR absorption spectroscopy was used to confirm successful suspensions and obtain the mass concentration of the nanoparticles using an extinction coefficient of $\varepsilon_{632}$=0.036 mg/(L cm).

Sensor Screening. High throughput screening of the sensor library against the steroid panel was performed using a customized nIR microscope, which consists of a Zeiss Axio Vision inverted Microscope body with a 20× objective, coupled to a Acton SP2500 spectrometer and liquid nitrogen cooled InGaAs 1D detector (Princeton Instruments). In a 96 well plate, one SWNT sensor (1 mg/L) and one steroid (100 μM) were mixed in a final volume of 150 μL in 1× PBS with 2 vol % DMSO and incubated for 1 hour in each well. The samples were then illuminated by a 150 mW 785 nm photodiode laser (B&W Tek Inc.), and fluorescence emission spectra were collected from 950 to 1250 nm. The fluorescence spectra were deconvoluted into individual peaks corresponding to single SWNT chiralities according to a previously reported algorithm. See, for example, Zhang, J. et al. Molecular recognition using corona phase complexes made of synthetic polymers adsorbed on carbon nanotubes. *Nat. Nanotechnol.* 8, 959-68 (2013), which is incorporated by reference in its entirety. Peak position and intensities of each sensor-steroid pair were compared to a sensor-blank control to calculate the sensor response. The most promising candidates were identified and studied further.

Hydrogel Fabrication and Characterization. SWNT were encapsulated in a hydrogel matrix using a modified version of a previously reported protocol. See, for example, Iverson, N. M. et al. Quantitative tissue spectroscopy of near infrared fluorescent nanosensor implants. *J. Biomed. Nanotechnol.* 12, 1035-1047 (2016), which is incorporated by reference in its entirety. Briefly PEGDA (100 mg/L), dispersed SWNT (10 mg/L), and 2-hydroxy-4'-(2-hydroxyethoxy)-2-methylpriophenone (0.175 mg/mL) were mixed in 1× PBS. The mixture was placed into glass molds. After a 30 minute incubation in a nitrogen atmosphere, the molds were crosslinked under 365 nm ultraviolet light (UVP Blak-Ray XX-15BLB, 15 W) for 1 hour. The hydrogels were incubated in 1× PBS, with a replacement with fresh 1× PBS after 48 hours to remove unencapsulated SWNT and excess polymer.

Hydrogels were cut to 5×5×1 mm sections. Hydrogels were either used directly after fabrication or were placed into 6-8 kDa dialysis bags with a volume of 300 µL 1× PBS.

Fluorescence imaging on hydrogels were performed using a 2D InGaAs camera (Princeton Instruments) coupled to a Nikon AF Micro-Nikkor 60 mm 4/2.8D lens. The hydrogels were illuminated under a 785 nm Invictus laser (Kaiser). The optical window from 1075-1200 nm was monitored using a 1075 nm longpass filter and 1200 nm shortpass filter (Edmund Optics). To test progesterone responsivity, unencapsulated hydrogels were placed in 6-well plates and exposed to varying concentrations of progesterone. Hydrogels encapsulated in 6-8 kDa dialysis bags (Spectrum Labs) were imaged inside of transparent, 20 mL scintillation vials with 100 µM progesterone solution in 2% DMSO and 1× PBS.

Excitation-emission maps were constructed by tracking the fluorescence spectrum from 950-1250 nm while stepping the excitation from 500-800 nm in 5 nm increments. A 1 W broadband white laser was coupled to a tunable filter with a 2 nm bandwidth (Photon Etc.) and fed to the aforementioned custom built NIR microscope array.

In vivo implantation and imaging. These procedures were reviewed and approved by the Committee on Animal Care at MIT. Prior to implantation, hydrogels were incubated in 2% DMSO and 1× PBS, with or without 100 µm progesterone for three hours. The hydrogels were then sterilized under 365 nm UV light (UVP Blak-Ray XX-15BLB, 15 W) for 10 minutes.

Female 7 week old SKH-1E mice (Charles River Laboratory) were anesthetized under 2% isoflurane gas for 15 minutes. Once unresponsive to a toe pinch, the implantation site was sterilized using alternating washes with iopovidone and 70% ethanol repeated thrice. Hydrogels were placed subcutaneously in the dorsal side of the animal. The wound was closed with nylon sutures. Animals were imaged under 2% isoflurane using a 2D InGaAs camera coupled to a Nikon AF Micro-Nikkor 60 mm 4/2.8D lens, 1075 nm longpass filter, and 1200 nm shortpass filter. The mice were illuminated under a 785 nm Invictus laser dispersed over the surface of the animal to a power density of 10 mW/cm². After their experimental lifetime, mice were euthanized by $CO_2$ asphyxiation.

Other embodiments are within the scope of the following claims.

What is claimed is:

1. A composition, comprising:
   a complex, wherein the complex includes:
      a nanostructure; and
      a polymer, the polymer adsorbed on the nanostructure and the polymer being free from selective binding to an analyte in the absence of being adsorbed on the nanostructure, wherein the polymer is a heteropolymer including a hydrophobic region and a hydrophilic region and the polymer includes a template moiety; and
   a selective binding site associated with the complex, the selectivity of the selective binding site being dependent on the template moiety.

2. The composition of claim 1, wherein the nanostructure is a photoluminescent nanostructure.

3. The composition of claim 2, wherein the photoluminescent nanostructure is a nanotube, a carbon nanotube, or a single-walled carbon nanotube.

4. The composition of claim 1, wherein the polymer includes a polystyrene.

5. The composition of claim 4, wherein the polymer includes a polyacrylate.

6. The composition of claim 1, wherein the polymer is a polyacrylate-polystyrene copolymer.

7. The composition of claim 1, wherein the polymer is covalently bonded to one or more of the template moiety.

8. The composition of claim 1, wherein the template moiety includes a steroid moiety.

9. The composition of claim 1, wherein the polymer has the structure:

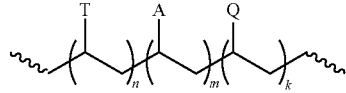

wherein n is 1 to 500, m is an integer from 0 to 500, and k is an integer from 1 to 500;
T is a template moiety;
A is a hydrophilic moiety; and
Q is a group that associates with the nanostructure.

10. The composition of claim 9, wherein Q is an aromatic group.

11. The composition of claim 1, wherein the template is a cortisol, testosterone, dehydroepiandrosterone (DHEA), pregnenolone, estradiol, prednisone, corticosterone, progesterone, cortisone, aldosterone or prednisolone moiety.

12. The composition of claim 1, wherein the analyte is cortisol, testosterone, dehydroepiandrosterone (DHEA), pregnenolone, estradiol, prednisone, corticosterone, progesterone, cortisone, aldosterone or prednisolone.

13. A sensor including a matrix and the composition of claim 1 suspended in the matrix.

14. A method for analyzing a sample for an analyte, comprising:
   providing a composition of claim 1;
   exposing the composition to a sample;
   monitoring a property of the composition; and
   determining a presence of an analyte in the sample based on the property.

15. The method of claim 14, wherein the sample includes a gas, a liquid or a solid.

16. The method of claim 14, wherein the sample is a biological fluid.

17. The method of claim 14, wherein the property is an emission, emission intensity, or an emission wavelength.

18. The method of claim 14, wherein exposing the composition to a sample includes inserting the composition into an animal, a plant, or a fungus.

19. The method of claim 14, wherein exposing the composition to a sample includes incubating the composition with a microorganism, a virus, a cell line, or an in vitro model system.

20. The method of claim 14, wherein determining the presence of an analyte includes determining the absence of the analyte, or determining the concentration of the analyte.

21. The method of claim 14, wherein monitoring a property of the composition includes creating an image.

22. A method of making a composition including templating a composition that selective binds an analyte, wherein templating includes contacting a nanostructure, and a polymer, the polymer adsorbed on the nanostructure and the polymer being free from selective binding to an analyte in the absence of being adsorbed on the nanostructure, wherein the polymer is a heteropolymer including a hydrophobic region and a hydrophilic region and the polymer includes a template moiety.

23. A system comprising:
    the composition claim 1;
    an electromagnetic radiation source having an excitation wavelength directed at the composition; and
    a detector configured to receive an emission wavelength from the composition.

* * * * *